(12) United States Patent
Dorsch et al.

(10) Patent No.: US 8,778,927 B2
(45) Date of Patent: Jul. 15, 2014

(54) SMOOTHENED ANTAGONISM FOR THE TREATMENT OF HEDGEHOG PATHWAY-RELATED DISORDERS

(75) Inventors: Marion Dorsch, Jamaica Plain, MA (US); John E. Monahan, Walpole, MA (US); Michael Patrick Morrissey, Watertown, MA (US); Shifeng Pan, San Diego, CA (US); Juliet Williams, London (GB)

(73) Assignee: Novartis AG, Basel (CH)

( * ) Notice: Subject to any disclaimer, the term of this patent is extended or adjusted under 35 U.S.C. 154(b) by 134 days.

(21) Appl. No.: 13/119,072

(22) PCT Filed: Sep. 28, 2009

(86) PCT No.: PCT/EP2009/062537
§ 371 (c)(1), (2), (4) Date: Mar. 15, 2011

(87) PCT Pub. No.: WO2010/037715
PCT Pub. Date: Apr. 8, 2010

(65) Prior Publication Data
US 2011/0183962 A1 Jul. 28, 2011

Related U.S. Application Data

(60) Provisional application No. 61/101,851, filed on Oct. 1, 2008, provisional application No. 61/101,858, filed on Oct. 1, 2008.

(51) Int. Cl.
*A61K 31/00* (2006.01)
(52) U.S. Cl.
USPC .................................. 514/211.08; 514/235.5
(58) Field of Classification Search
USPC ........................................ 514/211.08, 235.5
See application file for complete search history.

(56) References Cited

U.S. PATENT DOCUMENTS 4,681,893 A * 7/1987 Roth .............................. 514/422
7,799,782 B2 * 9/2010 Munson et al. ............. 514/234.5
8,178,563 B2 * 5/2012 Gao et al. ...................... 514/352
8,217,035 B2 * 7/2012 Burger et al. ............... 514/232.2
2008/0194579 A1 * 8/2008 Garcia-Echeverria et al. ........................ 514/253.03

FOREIGN PATENT DOCUMENTS

| WO | WO 03/11219 | 2/2003 |
| WO | WO 2005/094864 | 10/2005 |
| WO | WO 2006/028958 | 3/2006 |
| WO | 2006122806 | 11/2006 |
| WO | 200784786 | 7/2007 |
| WO | WO 2007/120827 | 10/2007 |
| WO | WO 2007/131201 | 11/2007 |
| WO | 2007139492 | 12/2007 |
| WO | WO 2008/110611 | 9/2008 |

OTHER PUBLICATIONS

Clement V et al: "HEDGEHOG-GLI1 signaling regulates human glioma growth, cancer stem cell self-renewal and trumorigenicity". Current Biology 2007; 17(2):165-172.
Bar EE, et al: "Cyclopamine-mediated hedgehog pathway inhibition depletes stem-like cancer cells in glioblastoma" Stem Cells, Oct. 25, 2007 (10):2524-33.
Hahn H et al: "Patched Target Igf2 is indispensible for the formation of Medulloblastoma and Rhabodmyosarcoma" Journal Biological Chemistry 2000, 275: 28341-28344.
Riobo et al: "Phosphoinositide 3-kinase and AKT are essential for Sonci Hedgehog signaling" PNAS. 2006;103 (12):4505-4510.

* cited by examiner

*Primary Examiner* — Rei-tsang Shiao
(74) *Attorney, Agent, or Firm* — Matthew Mulkeen

(57) ABSTRACT

The invention provides methods for modulating, e.g., antagonizing, the activity of the Hedgehog signaling pathway, and for treating Hedgehog related disorders such as cancers (e.g., medulloblastoma). In particular, the invention provides methods for inhibiting aberrant growth states resulting from phenotypes such as Ptch loss-of-function, Hedgehog gain-of-function, smoothened gain-of-function or Gli gain-of-function by administering to a mammal combinations of Smoothened inhibitors (e.g., a compound of Formula I, Formula II, or Formula III, or any of the compounds listed herein or incorporated by reference) and cholesterol biosynthesis pathway inhibitors (e.g., statins), Gli inhibitors, and/or Phosphatidylinositol 3-kinase (PI3K) inhibitors.

12 Claims, 7 Drawing Sheets

SMOOTHENED ANTAGONISM FOR THE TREATMENT OF HEDGEHOG PATHWAY-RELATED DISORDERS

This is a National Stage of International Application No. PCT/EP2009/062537 filed on Sept. 28, 2009, which claims benefit of U.S. Provisional Application No. 61,101,851 filed Oct. 1, 2008 and U.S. Provisional Application No. 61/101,858 filed Oct. 1, 2008, which in its entirety are herein incorporated by reference.

BACKGROUND OF THE INVENTION

Hedgehog (Hh) signaling was first identified in Drosophila as an important regulatory mechanism for embryonic pattern formation, or the process by which embryonic cells form ordered spatial arrangements of differentiated tissues. (Nusslein-Volhard et al. (1980) Nature 287, 795-801) In mammalian cells, three Hedgehog genes, Sonic Hedgehog (Shh), India Hedgehog (Ihh) and Desert Hedgehog (Dhh), have been identified. Hedgehog genes encode secreted proteins, which undergo post-translational modifications, including autocatalytic cleavage and lipid modification (palmitoylation) at the N-terminus and cholesterol modification of the C-terminus.

The lipid-modified N-terminal Hedgehog protein triggers the signaling activity of the protein pathway, and cell to cell communication is engendered by the dispatch of soluble Hedgehog protein from a signaling cell and receipt by a responding cell. In responding cells, the 12-pass transmembrane receptor Patched (Ptch) acts as negative regulator of Hh signaling and the 7-pass transmembrane protein Smoothened (Smo) acts as a positive regulator of Hh signaling. At resting state, free Ptch (i.e., unbound by Hh) substoichiometrically suppresses pathway activity induced by Smo (Taipale et al. (2002) Nature 418: 892); upon binding ligand Hh protein, however, repression of Smo is relieved, and the resulting signaling cascade leads to the activation and nuclear translocation of Gli transcription factors (Gli1, Gli2 and Gli3).

Downstream target genes of Hh signaling transcription include Wnts, TGFβ, and Gli1, which are elements of the positive and negative regulatory feedback loop. Several cell-cycle and proliferation regulatory genes, such as c-myc, cyclin D and E are also among the target genes of Hh signaling.

Hh signaling is known to regulate a diverse range of biological processes, such as cellular proliferation, differentiation, and organ formation in a tissue specific and dose dependent manner. In the development of neural tubes, Shh is expressed in the floorplate and directs the differentiation of specific subtypes of neurons, including motor and dopaminergic neurons. Hh is also known to regulate the proliferation of neuronal progenitor cells, such as cerebella granule cells and neural stem cells. In the developing intestinal tract, a low-level of Hh signaling is required for pancreatic development, while a high-level of Hh signaling blocks pancreatic organogenesis. Hh is also known to play important roles in stem cell proliferation and organogenesis in skin, prostate, testis and bone marrow.

Normally, Hh signaling is strictly controlled during cellular proliferation, differentiation and embryonic pattern formation. However, aberrant activity of the Hedgehog signaling pathway, due to mutations that constitutively activate the pathway, for instance, may have pathological consequences. By way of example, loss-of-function mutations of Patched are found in Gorlin's syndrome (a hereditary syndrome with high risk of skin and brain cancers, also known as Basal Cell Nevus Syndrome (BCNS)); and gain-of-function mutations of Smo and Gli are linked to basal cell carcinoma and glioblastoma. Basal cell carcinoma (BCC) is the most common form of skin cancer, affecting more than 90,000 Americans each year.

Constitutive activation of Hh has been found to promote tumorigenesis in BCC, medulloblastoma (the most common childhood brain tumor), rhabdomyosarcoma, pancreatic cancer, small cell lung cancer, prostate cancer and breast cancer. Besides the roles in tumorigenesis, Hh signaling is also implicated in the metastasis of prostate cancer. Hh signaling may be involved in many additional types of tumor types and such links are expected to continue to be discovered; this is an area of active research in many cancer centers around the world.

Proliferation of these cancer cells requires Hh pathway activation, and blocking Hh signaling pathways often inhibits cancer cell proliferation. Indeed, Hh antagonist cyclopamine and anti-Gli1 siRNA can effectively block the proliferation of these cancer cells, and can reduce tumor size in Xenograft models, suggesting that Hh antagonists, alone or in combination with other agents, could provide new chemotherapeutic regimens for the treatment of these cancers. Hh antagonist cyclopamine has been shown to suppress the metastasis of prostate cancer in animal models.

Evidence that constitutive activation of Smo results in cancers (e.g., BCC), and that Smo may be oncogenic upon its release from inhibition by Ptch, suggests utility of Smo antagonists as therapeutic agents in the treatment of such disorders. (Stone et al. (1996) Nature 384: 129). Accordingly, molecules that modulate the activity of the Hedgehog signaling pathway, e.g., which modulate Smo activity, are therapeutically useful.

SUMMARY OF THE INVENTION

The present invention relates generally to the diagnosis and treatment of pathologies relating to the Hedgehog pathway (defined below and referred to herein as "Hedgehog-related disorder(s)"), including but not limited to tumor formation, cancer, neoplasia, and non-malignant hyperproliferative disorders, and more particularly to methods of inhibiting tumorigenesis, tumor growth and tumor survival, using agents known to inhibit the Hedgehog and Smo signaling pathway (e.g., Smoothened inhibitors) in combination with (i) cholesterol biosynthesis pathway inhibitors (e.g., statins); (ii) Gli inhibitors; and/or (iii) Phosphatidylinositol 3-kinase (PI3K) inhibitors. Smoothened inhibitors is a class defined herein and includes, but is not limited to, cyclopamine, jervine, compounds of Formula I (e.g., a compound of Formulae (Ia), (Ib) or (Ic)), compounds of Formula II, compounds of Formula III, any of the anti-smoothened compounds individually listed herein, anti-Smo antibodies, anti-Smo inhibitory nucleic acids (e.g., anti-Smo siRNAs), and other known anti-Smoothened agents in the art and/or incorporated herein by reference. Phosphatidylinositol 3-kinase (PI3K) inhibitors is also a class defined herein and includes, but is not limited to, compounds of Formula A, as well as lipid kinase inhibitors and anti-PI3K inhibitory nucleotides (e.g., RNAi).

The methods and compounds of the present invention relate to inhibiting activation of the Hedgehog signaling pathway, e.g., by inhibiting aberrant growth states resulting from phenotypes such as Ptch loss-of-function, Hedgehog gain-of-function, Smoothened gain-of-function or Gli gain-of-function, and comprise contacting the cell with a combination of agents known to inhibit the Hedgehog and Smo signaling pathway, e.g., Smoothened inhibitors, and cholesterol biosynthesis inhibitors (e.g., statins); Gli inhibitors; and/or Phosphatidylinositol 3-kinase (PI3K) inhibitors in a sufficient amount to agonize a normal Ptch activity, antagonize a normal Hedgehog activity, or antagonize smoothened activity (e.g., to reverse or control the aberrant growth state).

One aspect of the present invention includes methods employing compounds for inhibiting Smo-dependent pathway activation (e.g., when Smo is activated by the presence of the Hedgehog ligand). Another aspect of the present invention includes methods employing compounds for inhibiting Hedgehog (ligand)-independent pathway activation. In certain embodiments, the present methods can be used to counteract the phenotypic effects of unwanted activation of a Hedgehog pathway, such as resulting from Hedgehog gain-of-function, Ptch loss-of-function or smoothened gain-of-function mutations, whether the activation is in the presence or absence of the Hedgehog ligand. For instance, a method of the invention can involve contacting a cell (in vitro or in vivo) with a Smo antagonist, such as a Smoothened inhibitor, in combination with cholesterol biosynthesis pathway inhibitors (e.g., statins), Gli inhibitors, and/or Phosphatidylinositol 3-kinase (PI3K) inhibitors, in an amount sufficient to antagonize smoothened-dependent or smoothened-independent (i.e., if activation occurs downstream of smoothened) Hedgehog pathway signaling, in the presence or absence of the Hedgehog ligand.

Certain embodiments of the present invention provide methods for inhibiting the synthesis, expression, production, stabilization, phosphorylation, relocation within the cell, and/or activity of a Smo protein in a cell in vitro or in vivo, comprising contacting said cell with, or introducing into said cell, a combination of Smoothened inhibitors and cholesterol biosynthesis pathway inhibitors (e.g., statins), Gli inhibitors, and/or Phosphatidylinositol 3-kinase (PI3K) inhibitors. The combination of Smoothened inhibitors and cholesterol biosynthesis pathway inhibitors (e.g., statins), Gli inhibitors, and/or Phosphatidylinositol 3-kinase (PI3K) inhibitors can be administered simultaneously or sequentially. For instance, the cholesterol biosynthesis pathway inhibitors (e.g., statins), Gli inhibitors, and/or Phosphatidylinositol 3-kinase (PI3K) inhibitors can be administered in instances after resistant tumors develop in the presence of Smo inhibitors.

In certain embodiments, proteins downstream of Smo in the Hedgehog signaling pathway (e.g., Gli) are also inhibited in a cell in vitro or in vivo. For example, the synthesis, expression, production, stabilization, phosphorylation, relocation within the cell, and/or activity of Gli protein(s) may be inhibited, in addition to the inhibition of Smoothened as described above, comprising contacting said cell with, or introducing into said cell, a combination of Smoothened inhibitors and cholesterol biosynthesis pathway inhibitors (e.g., statins), Gli inhibitors, and/or Phosphatidylinositol 3-kinase (PI3K) inhibitors. In certain embodiments, the Hedgehog pathway may still be active in a cell despite having been previously subjected to a Smoothened antagonist (e.g., as is the case with resistant tumors), because the pathway is activated downstream of Smo (e.g., with Gli). In other embodiments, a cell has not been previously subjected to a Smoothened antagonist.

The methods of the present invention may be used to regulate proliferation and/or differentiation of cells in vitro and/or in vivo, e.g., in the formation of tissue from stem cells, or to prevent the growth of hyperproliferative cells. In another particular embodiment, contacting the cell with—or introducing into the cell—a combination of Smoothened inhibitors and cholesterol biosynthesis pathway inhibitors (e.g., statins), Gli inhibitors, and/or Phosphatidylinositol 3-kinase (PI3K) inhibitors results in inhibition of cellular proliferation, inhibition of tumor cell growth and/or survival, and/or inhibition of tumorigenesis. Thus, another particular embodiment provides methods for inhibiting and/or antagonizing the Hh pathway by employing combination methods of the invention in tumor cells. In certain embodiments, said cellular proliferation, tumor cell growth and/or survival, and/or tumorigenesis is associated with resistant tumors. In other embodiments, said cellular proliferation, tumor cell growth and/or survival, and/or tumorigenesis is associated with sensitive tumors.

The combinations of the invention may be administered in certain embodiments to a patient afflicted by sensitive tumors. Said combinations may be administered in certain other embodiments to a patient afflicted by resistant tumors.

Tumor cells as described herein, which the combinations of the invention may be employed to treat, may be apoptosis-resistant, may resist conventional anti-cancer regimens, and/or may be resistant tumors as defined herein. Resistant tumors may, for instance, arise via genetic changes which lead to the reactivation of the Hedgehog pathway despite the presence of Smo inhibitors. Examples are Smo mutations that interfere with inhibitor binding, and/or mutations in genes downstream of Smo that lead to reactivation of the Hedgehog pathway (e.g., sufu, Gli1, Gli2). In these instances of resistant tumors and tumors which do not succumb to conventional anti-cancer regimens, the combinations of the invention can induce tumor cells to undergo senescence, apoptosis, or necrosis. The administration of said combinations can result in tumor cell death and prevention from metastasis.

The methods of the present invention may employ combinations of Smoothened inhibitors as formulated as pharmaceutical preparations comprising a pharmaceutically acceptable excipient or carrier, and cholesterol biosynthesis pathway inhibitors (e.g., statins), Gli inhibitors, and/or Phosphatidylinositol 3-kinase (PI3K) inhibitors. Likewise, said cholesterol biosynthesis pathway inhibitors (e.g., statins), Gli inhibitors, and/or Phosphatidylinositol 3-kinase (PI3K) inhibitors may be formulated as pharmaceutical preparations comprising a pharmaceutically acceptable excipient or carrier as well. Said combinations may be administered to a patient to treat conditions involving unwanted cell proliferation such as cancers and/or tumors (such as medulloblastoma, basal cell carcinoma, etc.), and non-malignant hyperproliferative disorders. Said combinations may be administered in certain embodiments to a patient afflicted by sensitive tumors. Said combinations may be administered in certain other embodiments to a patient afflicted by resistant tumors.

Other aspects of the invention provide methods of diagnosing, preventing and/or treating cellular debilitations, derangements, and/or dysfunctions; hyperplastic, hyperproliferative and/or cancerous disease states; and/or metastasis of tumor cells, in a mammal characterized by the presence and/or expression of a Smo gene or gene product (e.g., a Smo protein), comprising administering to a mammal combinations of Smoothened inhibitors and cholesterol biosynthesis pathway inhibitors (e.g., statins), Gli inhibitors, and/or Phosphatidylinositol 3-kinase (PI3K) inhibitors.

BRIEF DESCRIPTION OF THE FIGURES

As described in greater detail below.

As described in greater detail below.

As described in greater detail below.

DETAILED DESCRIPTION OF THE INVENTION

Figure 1:
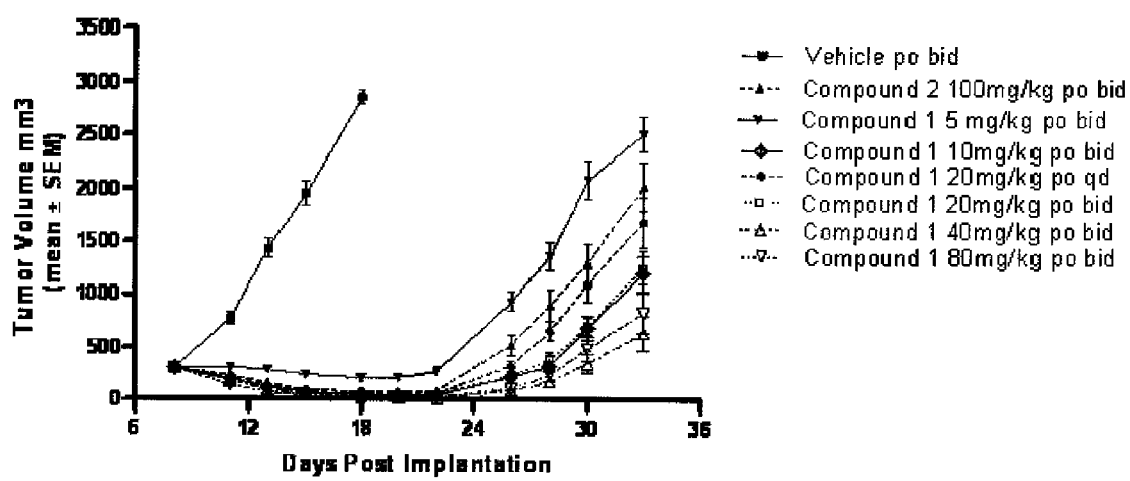
FIG. 1 shows the anti-tumor activity of Compounds 1 and 2 and resistance to Compounds 1 and 2 in the Ptch+/−p53−/− medulloblastoma allograft model following 25 days of treatment.

Smoothened inhibitors can include compounds, e.g., biarylcarboxamide compounds, of the formula (I):

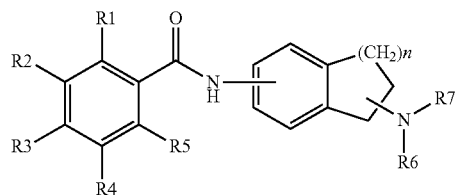

(I)

wherein
R2-C, R3-C, R4-C or R5-C may be replaced by N;
n is 1, 2 or 3;
R1 is carbocyclic aryl or heteroaryl;
R2, R3, R4 and R5 are independently hydrogen, lower alkyl, lower alkoxy, lower alkylthio, fluoro, chloro, bromo, amino, substituted amino, trifluoromethyl, acyloxy, alkylcarbonyl, trifluoromethoxy or cyano;
R6 is hydrogen, optionally substituted alkyl, carbocyclic or heterocyclic aryl-lower alkyl;
R7 is hydrogen, optionally substituted alkyl, carbocyclic aryl, heteroaryl, carbocyclic aryl-lower alkyl, heteroaryl-lower alkyl, or

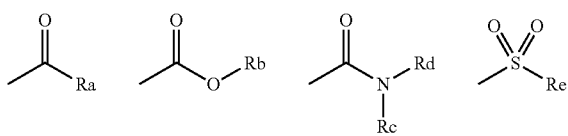

wherein
Ra is optionally substituted alkyl, cycloalkyl, aryl or heterocyclyl;
Rb is optionally substituted alkyl, cycloalkyl, aryl or heterocyclyl;
Rc and Rd are independently hydrogen, substituted alkyl, cycloalkyl, aryl; or
heterocyclyl; or Rc and Rd together represent lower alkylene or lower alkylene interrupted by O, S, N—(H, alkyl, arylalkyl);

Re is optionally substituted alkyl, cycloalkyl, aryl or heterocyclyl, amino or substituted amino;
and pharmaceutically acceptable salts thereof, and enantiomers thereof.

A preferred embodiment of the invention relates to compounds of Formula (Ia)

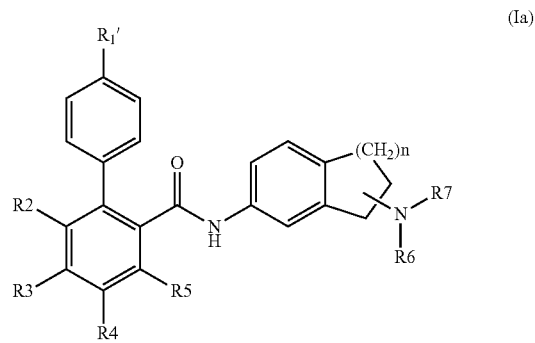

(Ia)

wherein R2-C, R3-C, R4-C or R5-C may be replaced by N;
wherein
R1' is hydrogen, fluoro, chloro, bromo, lower alkyl, cyano, methoxy, trifluoromethyl, trifluoromethoxy, dimethylamino;
R2 to R7 have meaning as defined for Formula I,
and pharmaceutically acceptable salts thereof, and enantiomers thereof.

Another preferred embodiment of the invention relates to compounds of Formula (Ib)

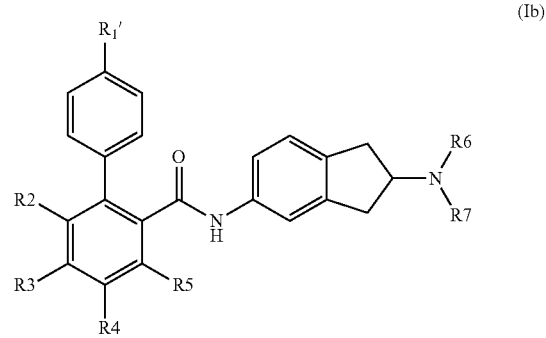

(Ib)

wherein
R1' is trifluoromethyl, chloro, fluoro;
R2 and R3 are independently hydrogen, C1-C4 alkyl, C1-C4-alkoxy, trifluoromethyl, chloro or fluoro;
R4 and R5 are hydrogen;
R6 is hydrogen or C1-C3 alkyl;
R7 is optionally substituted alkyl, carbocyclic aryl, heteroaryl, carbocyclic aryl-lower alkyl, heteroaryl-lower alkyl, or

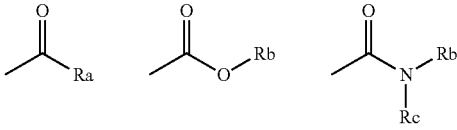

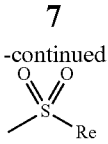

wherein

Ra is optionally substituted alkyl, cycloalkyl, aryl or heterocyclyl;

Rb is optionally substituted alkyl, cycloalkyl, aryl or heterocyclyl;

Rc and Rd are independently hydrogen, substituted alkyl, cycloalkyl, aryl; or heterocyclyl, or Rc and Rd together represent lower alkylene or lower alkylene interrupted by O, S, N—(H, alkyl, arylalkyl);

Re is optionally substituted alkyl, cycloalkyl, aryl or heterocyclyl, amino or substituted amino;

and pharmaceutically acceptable salts thereof, and enantiomers thereof.

Another preferred embodiment of the invention relates to compounds of Formula (Ib)

wherein

R1' is trifluoromethyl, chloro, fluoro;

R2 and R3 are independently hydrogen, C1-C4 alkyl, C1-C4-alkoxy, trifluoromethyl, chloro or fluoro;

R4 and R5 are hydrogen;

R6 is hydrogen;

R7 is optionally substituted alkyl, carbocyclic aryl, heteroaryl, carbocyclic aryl-lower alkyl or heteroaryl-lower alkyl;

and pharmaceutically acceptable salts thereof, and enantiomers thereof.

Another particularly preferred embodiment of the invention relates to compounds of Formula (Ic)

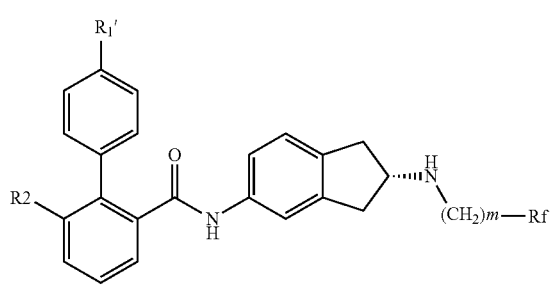

wherein

R1' is trifluoromethyl or chloro;

R2 is hydrogen or methyl;

m is 0 or 1;

Rf is carbocyclic or heterocyclic aryl;

and pharmaceutically acceptable salts thereof.

The combinations of the invention, depending on the nature of the substituents described herein, possess one or more asymmetric carbon atoms, and therefore exist as racemates, and the R and S enantiomer thereof. Preferred is the more active enantiomer, typically assigned the S configuration (at the carbon with the NR6R7 substituent).

Smoothened inhibitor compounds can also include compounds of Formula II:

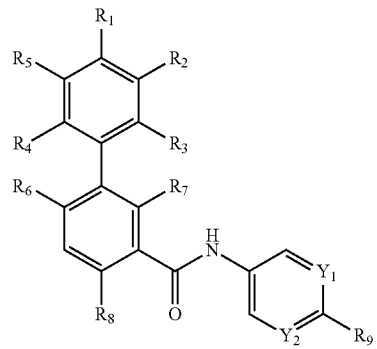

in which $Y_1$ and $Y_2$ are independently selected from N and $CR_{10}$; wherein $R_{10}$ is selected from hydrogen, halo, $C_{1-6}$alkyl, halo-substituted-$C_{1-6}$alkyl, $C_{1-6}$alkoxy, halosubstituted-$C_{1-6}$alkoxy and —OXNR$_{10a}$R$_{10b}$; wherein R$_{10a}$ and R$_{10b}$ are independently selected from hydrogen and $C_{1-6}$alkyl;

$R_1$ is selected from cyano, halo, $C_{1-6}$alkyl, halosubstituted-$C_{1-6}$alkyl, $C_{1-6}$alkoxy, halosubstituted-$C_{1-6}$alkoxy, $C_{6-10}$aryl, dimethyl-amino, $C_{1-6}$alkyl-sulfanyl and $C_{3-8}$heterocycloalkyl optionally substituted with up to 2 $C_{1-6}$alkyl radicals;

$R_2$ and $R_5$ are independently selected from hydrogen, cyano, halo, $C_{1-6}$alkyl, halosubstituted-$C_{1-6}$alkyl, $C_{1-6}$alkoxy, halosubstituted-$C_{1-6}$alkoxy and dimethylamino;

$R_3$ and $R_4$ are independently selected from hydrogen, halo, cyano, $C_{1-6}$alkyl, halosubstituted-$C_{1-6}$alkyl, $C_{1-6}$alkoxy and halosubstituted-$C_{1-6}$alkoxy; or either $R_1$ and $R_2$ or $R_1$ and $R_5$ together with the phenyl to which they are both attached form $C_{5-10}$heteroaryl;

$R_6$ and $R_7$ are independently selected from hydrogen, $C_{1-6}$alkyl, halosubstituted-$C_{1-6}$alkyl, $C_{1-6}$alkoxy and halosubstituted-$C_{1-6}$alkoxy; with the proviso that $R_6$ and $R_7$ are not both hydrogen;

$R_8$ is selected from hydrogen, halo, $C_{1-6}$alkyl, halosubstituted-$C_{1-6}$alkyl, $C_{1-6}$alkoxy and halosubstituted-$C_{1-6}$alkoxy;

$R_9$ is selected from —S(O)$_2$R$_{11}$, —C(O)R$_{11}$, —OR$_{11}$, —NR$_{12a}$R$_{12b}$ and —R$_{11}$; wherein R$_{11}$ is selected from aryl, heteroaryl, cycloalkyl and heterocycloalkyl; R$_{12a}$ and R$_{12b}$ are independently selected from $C_{1-6}$alkyl and hydroxy-substituted-$C_{1-6}$alkyl;

wherein said aryl, heteroaryl, cycloalkyl and heterocycloalkyl of R$_9$ can be optionally substituted with 1 to 3 radicals independently selected from $C_{1-6}$alkyl, halo substituted-$C_{1-6}$alkyl, $C_{1-6}$alkoxy, halosubstituted-$C_{1-6}$alkoxy, $C_{6-10}$aryl-$C_{0-4}$alkyl, $C_{5-10}$heteroaryl-$C_{0-4}$alkyl, $C_{3-12}$cycloalkyl and $C_{3-8}$heterocycloalkyl;

wherein said aryl-alkyl substituent of R$_9$ is optionally substituted with 1 to 3 radicals independently selected from halo, $C_{1-6}$alkyl, halosubstituted-$C_{1-6}$alkyl, $C_{1-6}$alkoxy, halo substituted-$C_{1-6}$alkoxy and methyl-piperazinyl; and the N-oxide derivatives, prodrug derivatives, protected derivatives, individual isomers and mixture of isomers thereof; and the pharmaceutically acceptable salts and solvates (e.g. hydrates) of such compounds.

Preferred compounds of Formula II are selected from 4'-cyano-6-methyl-biphenyl-3-carboxylic acid [4-(morpholine-4-sulfonyl)-phenyl]-amide, 4'-cyano-6-methyl-biphenyl-3-carboxylic acid [6-(2,6-dimethyl-morpholin-4-yl)-pyridin-3-yl]-amide, 4'-Cyano-2-methyl-biphenyl-3-carboxylic acid (6-azepan-1-yl-pyridin-3-yl)-amide, 4'-Methoxy-2-methyl-biphenyl-3-carboxylic acid (6-azepan-1-yl-pyridin-3-yl)-amide, 4'-Methoxy-2-methyl-biphenyl-3-carboxylic acid (4-cyclohexyl-phenyl)-amide, 4'-Methoxy-2-methyl-biphenyl-3-carboxylic acid [6-(2-methyl-morpholin-4-yl)-pyridin-3-yl]-amide, 4'-Dimethylamino-2-methyl-biphenyl-3-carboxylic acid (4-cyclohexyl-phenyl)-amide, 4'-Dimethylamino-2-methyl-biphenyl-3-carboxylic acid (4-morpholin-4-yl-phenyl)-amide, 6-Chloro-4'-dimethylamino-biphenyl-3-carboxylic acid (6-[1,4]oxazepan-4-yl-pyridin-3-yl)-amide, 6-Chloro-4'-dimethylamino-biphenyl-3-carboxylic acid (6-morpholin-4-yl-pyridin-3-yl)-amide, 6-Chloro-4'-dimethylamino-biphenyl-3-carboxylic acid (6-azepan-1-yl-pyridin-3-yl)-amide, 6-Chloro-4'-methoxy-biphenyl-3-carboxylic acid [6-(2-methyl-morpholin-4-yl)-pyridin-3-yl]-amide, 6-Chloro-4'-methoxy-biphenyl-3-carboxylic acid (6-[1,4]oxazepan-4-yl-pyridin-3-yl)-amide, 6-Chloro-4'-methoxy-biphenyl-3-carboxylic acid (6-azepan-1-yl-pyridin-3-yl)-amide, 6-Chloro-4'-methoxy-biphenyl-3-carboxylic acid (6-morpholin-4-yl-pyridin-3-yl)-amide, 4'-Methoxy-6-methyl-biphenyl-3-carboxylic acid (6-morpholin-4-yl-pyridin-3-yl)-amide, 4'-Methoxy-6-methyl-biphenyl-3-carboxylic acid (6-[1,4]oxazepan-4-yl-pyridin-3-yl)-amide, 4'-Methoxy-6-methyl-biphenyl-3-carboxylic acid [6-(2-methyl-morpholin-4-yl)-pyridin-3-yl]-amide, 4'-Dimethylamino-6-methyl-biphenyl-3-carboxylic acid [6-(2-methyl-morpholin-4-yl)-pyridin-3-yl]-amide, 4'-Dimethylamino-6-methyl-biphenyl-3-carboxylic acid (6-[1,4]oxazepan-4-yl-pyridin-3-yl)-amide, 4'-Dimethylamino-6-methyl-biphenyl-3-carboxylic acid (6-morpholin-4-yl-pyridin-3-yl)-amide, 4'-Methoxy-6-methyl-biphenyl-3-carboxylic acid (6-azepan-1-yl-pyridin-3-yl)-amide, 4'-Ethoxy-6-methyl-biphenyl-3-carboxylic acid (6-azepan-1-yl-pyridin-3-yl)-amide, 6-Methyl-4'-methylsulfanyl-biphenyl-3-carboxylic acid (6-azepan-1-yl-pyridin-3-yl)-amide, 4'-Dimethylamino-6-methyl-biphenyl-3-carboxylic acid (6-azepan-1-yl-pyridin-3-yl)-amide, 6-Methyl-[1,1'; 4',1"]terphenyl-3-carboxylic acid (6-azepan-1-yl-pyridin-3-yl)-amide, 3'-Chloro-6-methyl-biphenyl-3-carboxylic acid (6-azepan-1-yl-pyridin-3-yl)-amide, 2',4'-Dichloro-6-methyl-biphenyl-3-carboxylic acid (6-azepan-1-yl-pyridin-3-yl)-amide, 2'-Chloro-6-methyl-biphenyl-3-carboxylic acid (6-azepan-1-yl-pyridin-3-yl)-amide, 3'-Chloro-6-methyl-biphenyl-3-carboxylic acid (6-azepan-1-yl-pyridin-3-yl)-amide, 3',4'-Dichloro-6-methyl-biphenyl-3-carboxylic acid (6-azepan-1-yl-pyridin-3-yl)-amide, 3'-Chloro-6-methyl-4'-trifluoromethyl-biphenyl-3-carboxylic acid (6-azepan-1-yl-pyridin-3-yl)-amide, 6,4'-Dimethyl-biphenyl-3-carboxylic acid (6-azepan-1-yl-pyridin-3-yl)-amide, 4'-Ethyl-6-methyl-biphenyl-3-carboxylic acid (6-azepan-1-yl-pyridin-3-yl)-amide, 4'-tert-Butyl-6-methyl-biphenyl-3-carboxylic acid (6-azepan-1-yl-pyridin-3-yl)-amide, 6-Methyl-4'-propyl-biphenyl-3-carboxylic acid (6-azepan-1-yl-pyridin-3-yl)-amide, 4'-Isobutyl-6-methyl-biphenyl-3-carboxylic acid (6-azepan-1-yl-pyridin-3-yl)-amide, 4'-Isopropyl-6-methyl-biphenyl-3-carboxylic acid (6-azepan-1-yl-pyridin-3-yl)-amide, 6,2',6'-Trimethyl-biphenyl-3-carboxylic acid (6-azepan-1-yl-pyridin-3-yl)-amide, 6,2',3'-Trimethyl-biphenyl-3-carboxylic acid (6-azepan-1-yl-pyridin-3-yl)-amide, 6-Methyl-4'-trifluoromethyl-biphenyl-3-carboxylic acid (6-azepan-1-yl-pyridin-3-yl)-amide, 6-Methyl-3'-trifluoromethyl-biphenyl-3-carboxylic acid (6-azepan-1-yl-pyridin-3-yl)-amide, 6-Methyl-3',5'-bistrifluoromethyl-biphenyl-3-carboxylic acid (6-azepan-1-yl-pyridin-3-yl)-amide, 3'-Isopropoxy-6-methyl-biphenyl-3-carboxylic acid (6-azepan-1-yl-pyridin-3-yl)-amide, 3'-Ethoxy-6-methyl-biphenyl-3-carboxylic acid (6-azepan-1-yl-pyridin-3-yl)-amide, 2',6'-Dimethoxy-6-methyl-biphenyl-3-carboxylic acid (6-azepan-1-yl-pyridin-3-yl)-amide, 6-Methyl-4'-trifluoromethoxy-biphenyl-3-carboxylic acid (6-azepan-1-yl-pyridin-3-yl)-amide, 6-Methyl-3'-trifluoromethoxy-biphenyl-3-carboxylic acid (6-azepan-1-yl-pyridin-3-yl)-amide, 6-Methyl-biphenyl-3-carboxylic acid (4-morpholin-4-yl-phenyl)-amide, 4'-Methoxy-6-methyl-biphenyl-3-carboxylic acid (4-morpholin-4-yl-phenyl)-amide, 3'-Methoxy-6-methyl-biphenyl-3-carboxylic acid (4-morpholin-4-yl-phenyl)-amide, 4'-(2-Dimethylamino-ethoxy)-6-methyl-biphenyl-3-carboxylic acid (4-morpholin-4-yl-phenyl)-amide, 3'-Dimethylamino-6-methyl-biphenyl-3-carboxylic acid (4-morpholin-4-yl-phenyl)-amide, 4'-Fluoro-6-methyl-biphenyl-3-carboxylic acid (4-morpholin-4-yl-phenyl)-amide, 3'-Fluoro-6-methyl-biphenyl-3-carboxylic acid (4-morpholin-4-yl-phenyl)-amide, 2'-Fluoro-6-methyl-biphenyl-3-carboxylic acid (4-morpholin-4-yl-phenyl)-amide, 4-Methyl-N-(4-morpholin-4-yl-phenyl)-3-quinoxalin-6-yl-benzamide, 6-Methyl-4'-(4-methyl-piperazin-1-yl)-biphenyl-3-carboxylic acid (4-morpholin-4-yl-phenyl)-amide, 2'-Cyano-6-methyl-biphenyl-3-carboxylic acid (4-morpholin-4-yl-phenyl)-amide, 3'-Cyano-6-methyl-biphenyl-3-carboxylic acid (4-morpholin-4-yl-phenyl)-amide, 4'-Cyano-6-methyl-biphenyl-3-carboxylic acid (6-[1,4]oxazepan-4-yl-pyridin-3-yl)-amide, 4'-Cyano-6-methyl-biphenyl-3-carboxylic acid (6-azepan-1-yl-pyridin-3-yl)-amide, 4'-Cyano-6-methyl-biphenyl-3-carboxylic acid [6-(2-methyl-morpholin-4-yl)-pyridin-3-yl]-amide, 4'-Cyano-6-methyl-biphenyl-3-carboxylic acid (3,4,5,6-tetrahydro-2H-[1,2]bipyridinyl-5'-yl)-amide, 4'-Cyano-6-methyl-biphenyl-3-carboxylic acid (6-morpholin-4-yl-pyridin-3-yl)-amide, 4'-Cyano-6-methyl-biphenyl-3-carboxylic acid [6-(4-methyl-piperazin-1-yl)-pyridin-3-yl]-amide, 4'-Cyano-6-methyl-biphenyl-3-carboxylic acid (4-morpholin-4-yl-phenyl)-amide, 4'-Cyano-6-methyl-biphenyl-3-carboxylic acid (3-fluoro-4-morpholin-4-yl-phenyl)-amide, 4'-Cyano-6-methyl-biphenyl-3-carboxylic acid (3-chloro-4-morpholin-4-yl-phenyl)-amide, 4'-Cyano-6-methyl-biphenyl-3-carboxylic acid (3-bromo-4-morpholin-4-yl-phenyl)-amide, 4'-Cyano-6-methyl-biphenyl-3-carboxylic acid (3-methyl-4-morpholin-4-yl-phenyl)-amide, 4'-Cyano-6-methyl-biphenyl-3-carboxylic acid (4-morpholin-4-yl-3-trifluoromethyl-phenyl)-amide, 4'-Cyano-6-methyl-biphenyl-3-carboxylic acid (4-cyclohexyl-phenyl)-amide, 4'-Cyano-6-methyl-biphenyl-3-carboxylic acid biphenyl-4-ylamide, 4'-Cyano-6-methyl-biphenyl-3-carboxylic acid (4'-methoxy-biphenyl-4-yl)-amide, 4'-Cyano-6-methyl-biphenyl-3-carboxylic acid [4-(4-benzyl-piperazin-1-yl)-phenyl]-amide, 4'-Cyano-6-methyl-biphenyl-3-carboxylic acid [4-(piperidine-1-sulfonyl)-phenyl]-amide, 4'-Cyano-6-methyl-biphenyl-3-carboxylic acid [4-(pyrrolidine-1-sulfonyl)-phenyl]-amide, 4'-Cyano-6-methoxy-biphenyl-3-carboxylic acid (6-azepan-1-yl-pyridin-3-yl)-amide, 4'-Cyano-2-methoxy-biphenyl-3-carboxylic acid (6-azepan-1-yl-pyridin-3-yl)-amide, 4'-Cyano-2-methyl-biphenyl-3-carboxylic acid (6-azepan-1-yl-pyridin-3-yl)-amide, 3'-Fluoro-4'-methoxy-6-methyl-biphenyl-3-carboxylic acid (6-azepan-1-yl-pyridin-3-yl)-amide, 4'-Isopropoxy-6-methyl-biphenyl-3-carboxylic acid (6-azepan-1-yl-pyridin-3-yl)-amide, 4'-Butoxy-6-methyl-biphenyl-3-carboxylic acid (6-azepan-1-yl-pyridin-3-yl)-amide, 3'-Chloro-4'-methoxy-6-methyl-biphenyl-3-carboxylic acid (6-azepan-1-yl-pyridin-3-yl)-amide, 4'-Methoxy-6,3'-dimethyl-biphenyl-3-carboxylic acid (6-azepan-1-yl-pyridin-3-yl)-amide, 4'-Cyano-2-methyl-biphenyl-3-carboxylic acid [4-(piperidine-1-sulfonyl)-phenyl]-amide, 4'-Cyano-6-fluoro-biphenyl-3-carboxylic acid [4-(piperidine-1-sulfonyl)-phenyl]-amide, 6-Bromo-4'-cyano-biphenyl-3-carboxylic acid [4-(piperidine-1-sulfonyl)-phenyl]-amide, 4'-Cyano-6-methyl-biphenyl-3-carboxylic acid [6-(4-benzyl-[1,4]diazepan-1-yl)-pyridin-3-yl]-amide, 4'-Cyano-6-methyl-biphenyl-3-carboxylic acid [6-(4-thiophen-3-ylmethyl-[1,4]diazepan-1-yl)-pyridin-3-yl]-amide, 4'-Cyano-2-methyl-biphenyl-3-carboxylic acid [6-(2,6-dimethyl-morpholin-4-yl)-pyridin-3-yl]-amide,
4'-Methoxy-2-methyl-biphenyl-3-carboxylic acid [6-(2,6-dimethyl-morpholin-4-yl)-pyridin-3-yl]-amide, 2-Methyl-4'-trifluoromethyl-biphenyl-3-carboxylic acid [6-(2,6-dimethyl-morpholin-4-yl)-pyridin-3-yl]-amide, 2-Methyl-4'-trifluoromethoxy-biphenyl-3-carboxylic acid [6-(2,6-dimethyl-morpholin-4-yl)-pyridin-3-yl]-amide, 4'-Cyano-2-methyl-biphenyl-3-carboxylic acid [6-(2-methyl-morpholin-4-yl)-pyridin-3-yl]-amide, 4'-Cyano-2-fluoro-biphenyl-3-carboxylic acid [4-(piperidine-1-sulfonyl)-phenyl]-amide, 4'-Cyano-6-trifluoromethyl-biphenyl-3-carboxylic acid [4-(piperidine-1-sulfonyl)-phenyl]-amide, 4'-Cyano-6-methyl-biphenyl-3-carboxylic acid [6-(4-pyridin-4-ylmethyl-[1,4]diazepan-1-yl)-pyridin-3-yl]-amide, 4'-Cyano-6-methyl-biphenyl-3-carboxylic acid [6-(4-pyridin-3-ylmethyl-[1,4]diazepan-1-yl)-pyridin-3-yl]-amide, 4'-Cyano-6-methyl-biphenyl-3-carboxylic acid {6-[4-(2,6-dimethoxy-benzyl)-[1,4]diazepan-1-yl]-pyridin-3-yl}-amide, 4'-Cyano-6-methyl-biphenyl-3-carboxylic acid {6-[4-(2-ethoxy-benzyl)-[1,4]diazepan-1-yl]-pyridin-3-yl}-amide, 4'-Cyano-6-methyl-biphenyl-3-carboxylic acid (6-{4-[2-(4-methyl-piperazin-1-yl)-benzyl]-[1,4]diazepan-1-yl}-pyridin-3-yl)-amide, 4'-Cyano-6-methyl-biphenyl-3-carboxylic acid {6-[4-(4-methoxy-2,3-dimethyl-benzyl)-[1,4]diazepan-1-yl]-pyridin-3-yl}-amide, 4'-Cyano-6-methyl-biphenyl-3-carboxylic acid {6-[4-(2,3-dihydro-benzo[1,4]dioxin-6-ylmethyl)-[1,4]diazepan-1-yl]-pyridin-3-yl}-amide,
4'-Cyano-6-methyl-biphenyl-3-carboxylic acid [6-(4-pyridin-2-ylmethyl-[1,4]diazepan-1-yl)-pyridin-3-yl]-amide, 4'-Cyano-6-methyl-biphenyl-3-carboxylic acid [6-(4-benzo[1,3]dioxol-4-ylmethyl-[1,4]diazepan-1-yl)-pyridin-3-yl]-amide, 4'-Cyano-6-methyl-biphenyl-3-carboxylic acid {6-[4-(2-trifluoromethoxy-benzyl)-[1,4]diazepan-1-yl]-pyridin-3-yl}-amide, 4'-Cyano-6-methyl-biphenyl-3-carboxylic acid {6-[4-(2-dimethylamino-benzyl)-[1,4]diazepan-1-yl]-pyridin-3-yl}-amide, 4'-Cyano-6-methyl-biphenyl-3-carboxylic acid {6-[4-(2-chloro-5-trifluoromethyl-benzyl)-[1,4]diazepan-1-yl]-pyridin-3-yl}-amide, 4'-Cyano-6-methyl-biphenyl-3-carboxylic acid {6-[4-(2,3-difluoro-benzyl)-[1,4]diazepan-1-yl]-pyridin-3-yl}-amide, 4'-Cyano-6-methyl-biphenyl-3-carboxylic acid {6-[4-(2-chloro-4-fluoro-benzyl)-[1,4]diazepan-1-yl]-pyridin-3-yl}-amide, 4'-Cyano-6-methyl-biphenyl-3-carboxylic acid {6-[4-(2,6-difluoro-benzyl)-[1,4]diazepan-1-yl]-pyridin-3-yl}-amide, 2-Chloro-4'-cyano-biphenyl-3-carboxylic acid [4-(piperidine-1-sulfonyl)-phenyl]-amide, 4'-Cyano-6-trifluoromethyl-biphenyl-3-carboxylic acid [6-(2,6-dimethyl-morpholin-4-yl)-pyridin-3-yl]-amide, 2-Chloro-4'-cyano-biphenyl-3-carboxylic acid [6-(2,6-dimethyl-morpholin-4-yl)-pyridin-3-yl]-amide, 4'-Cyano-6-ethyl-biphenyl-3-carboxylic acid [6-(2,6-dimethyl-morpholin-4-yl)-pyridin-3-yl]-amide, 4'-Cyano-6-methyl-biphenyl-3-carboxylic acid {6-[4-(3-fluoro-benzyl)-piperazin-1-yl]-pyridin-3-yl}-amide, 4'-Cyano-6-methyl-biphenyl-3-carboxylic acid {6-[4-(2-trifluoromethoxy-benzyl)-piperazin-1-yl]-pyridin-3-yl}-amide, 4'-Cyano-6-methyl-biphenyl-3-carboxylic acid {6-[4-(3-chloro-benzyl)-piperazin-1-yl]-pyridin-3-yl}-amide, 4'-Cyano-6-methyl-biphenyl-3-carboxylic acid {6-[4-(4-isobutyl-benzyl)-piperazin-1-yl]-pyridin-3-yl}-amide,
4'-Cyano-6-methyl-biphenyl-3-carboxylic acid {6-[4-(4-tert-butyl-benzyl)-piperazin-1-yl]-pyridin-3-yl}-amide, 4'-Cyano-6-methyl-biphenyl-3-carboxylic acid {6-[4-(7-methoxy-benzo[1,3]dioxol-5-ylmethyl)-piperazin-1-yl]-pyridin-3-yl}-amide, 4'-Cyano-6-methyl-biphenyl-3-carboxylic acid [6-(4-benzyl-piperazin-1-yl)-pyridin-3-yl]-amide, 4'-Cyano-6-methyl-biphenyl-3-carboxylic acid [6-(4-pyridin-3-ylmethyl-piperazin-1-yl)-pyridin-3-yl]-amide, 4'-Cyano-6-methyl-biphenyl-3-carboxylic acid {6-[4-(4-difluoromethoxy-benzyl)-piperazin-1-yl]-pyridin-3-yl}-amide,
4'-Cyano-6-methyl-biphenyl-3-carboxylic acid {6-[4-(4-cyano-benzyl)-piperazin-1-yl]-pyridin-3-yl}-amide, 4'-Cyano-6-methyl-biphenyl-3-carboxylic acid [6-(4-quinolin-5-ylmethyl-piperazin-1-yl)-pyridin-3-yl]-amide, 4'-Cyano-6-methyl-biphenyl-3-carboxylic acid [6-(4-pyridin-4-ylmethyl-piperazin-1-yl)-pyridin-3-yl]-amide, 4'-Cyano-6-methyl-biphenyl-3-carboxylic acid [6-(4-pyridin-2-ylmethyl-piperazin-1-yl)-pyridin-3-yl]-amide, 4'-Cyano-6-methyl-biphenyl-3-carboxylic acid {6-[4-(4-imidazol-1-yl-benzyl)-piperazin-1-yl]-pyridin-3-yl}-amide, 4'-Cyano-6-methyl-biphenyl-3-carboxylic acid {6-[4-(3-cyano-benzyl)-piperazin-1-yl]-pyridin-3-yl}-amide, 4'-Cyano-6-methyl-biphenyl-3-carboxylic acid [6-(4-isoquinolin-5-ylmethyl-piperazin-1-yl)-pyridin-3-yl]-amide, (R)-2-methyl-N-(6-(2-methylmorpholino)pyridin-3-yl)-4'-(trifluoromethoxy)biphenyl-3-carboxamide, 4'-cyano-2-methyl-N-(6-sulfonylmorpholinopyridin-3-yl)biphenyl-3-carboxamide, (S)-4'-cyano-2-methyl-N-(6-(2-methylmorpholino)pyridin-3-yl)biphenyl-3-carboxamide, (R)-6-chloro-N-(6-(2-methylmorpholino)pyridin-3-yl)-4'-(trifluoromethoxy)biphenyl-3-carboxamide, 4'-cyano-2-methyl-N-(6-sulfinylmorpholinopyridin-3-yl)biphenyl-3-carboxamide, 4'-cyano-N-(6-(diisobutylamino)pyridin-3-yl)-2-methylbiphenyl-3-carboxamide, 4'-cyano-N-(2-((2S,6R)-2,6-dimethylmorpholino)pyrimidin-5-yl)-2-methylbiphenyl-3-carboxamide, N-(2-((2S,6R)-2,6-dimethylmorpholino)pyrimidin-5-yl)-2-methyl-4'-(trifluoromethyl)biphenyl-3-carboxamide, N-(2-((2S,6R)-2,6-dimethylmorpholino)pyrimidin-5-yl)-2-methyl-4'-(trifluoromethoxy)biphenyl-3-carboxamide, N-(2-(bis(2-hydroxyethyl)amino)pyrimidin-5-yl)-2-methyl-4'-(trifluoromethoxy)biphenyl-3-carboxamide, 2-methyl-N-(6-(tetrahydro-2H-pyran-4-yloxy)pyridin-3-yl)-4'-(trifluoromethoxy)biphenyl-3-carboxamide, N-(5-chloro-6-((2S,6R)-2,6-dimethylmorpholino)pyridin-3-yl)-2-methyl-4'-(trifluoromethoxy)biphenyl-3-carboxamide, N-(6-((2R,6S)-2,6-dimethyltetrahydro-2H-pyran-4-yl)pyridin-3-yl)-2-methyl-4'-(trifluoromethoxy)biphenyl-3-carboxamide,
N-(6-(4-ethylpiperazine-1-carbonyl)pyridin-3-yl)-2-methyl-4'-(trifluoromethoxy)biphenyl-3-carboxamide, 2-methyl-N-(6-(2-oxopiperazin-1-yl)pyridin-3-yl)-4'-(trifluoromethoxy)biphenyl-3-carboxamide, 2-methyl-N-(6-(1-(pyridin-4-ylmethyl)piperidin-4-yl)pyridin-3-yl)-4'-(trifluoromethoxy)biphenyl-3-carboxamide, 2-methyl-N-(6-(2-oxo-4-(pyridin-4-ylmethyl)piperazin-1-yl)pyridin-3-yl)-4'-(trifluoromethoxy)biphenyl-3-carboxamide, 2-methyl-N-(6-(1-(pyridin-4-ylmethyl)piperidin-3-yl)pyridin-3-yl)-4'-(trifluoromethoxy)biphenyl-3-carboxamide, N-(6-(1-ethylpiperidin-3-yl)pyridin-3-yl)-2-methyl-4'-(trifluoromethoxy)biphenyl-3-carboxamide and N-(6-((2R,6S)-2,6-dimethylmorpholino)pyridin-3-yl)-2-methyl-4'-(trifluoromethoxy)biphenyl-3-carboxamide and 2-Methyl-4'-trifluoromethoxy-biphenyl-3-carboxylic acid [6-(cis-2,6-dimethyl-morpholin-4-yl)-pyridin-3-yl]-amide, (also identified as Compound 1 in this document), which has the formula:

Compound 1

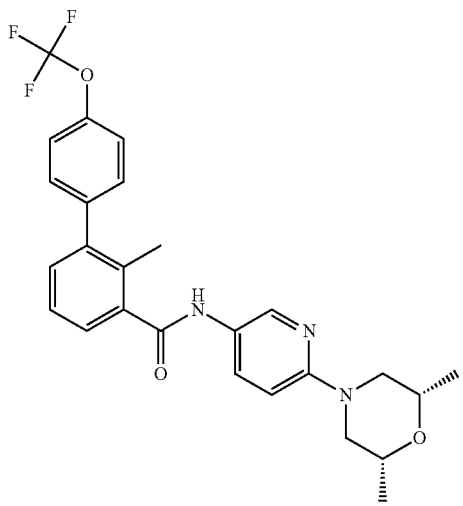

The above compounds of Formula II are further described in WO 2007/131201.

Smoothened inhibitor compounds can also include compounds of Formula III:

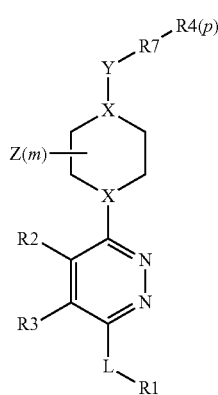

Formula III in which

R1 is a $C_{6-14}$ aryl group, or a 5-14 membered heteroaryl group which may be unsubstituted or substituted;

R2 and R3 are independently $C_{1-8}$ alkyl, $C_{1-8}$ alkylOH, or R2 and R3 form a fused $C_{3-14}$ cycloalkyl group;

L is a bond, $C_{1-8}$ alkylene, —C(O)O—, —C(O)NR9-, —$C_{1-8}$alkylOH—, —$C_{1-8}$haloalkyl-, —C(O)—, —NH— or —O—;

X and W are independently N or CR5, and at least one of X or W is N;

R7 is a $C_{6-14}$ aryl group, a 5-14 membered heteroaryl group, or a 3-14 membered cycloheteroalkyl group;

R4 is $C_{1-8}$ alkyl, $C_{2-8}$ alkenyl, $C_{3-14}$ cycloalkyl, a $C_{6-14}$ aryl group, a 5-14 membered heteroaryl group, a 3-14 membered cycloheteroalkyl group, $C_{1-8}$ alkoxy, halo, NR6R8, C(O)OR6, C(O)NR6R8, $C_{1-8}$haloalkyl, formyl, carbalkoxy, $C_{1-8}$alkylOH, C(O)R6, SO$_2$R6, C(O)NHC$_{1-8}$alkylR6, NR6R8, SO$_2$NR6R8, OCF$_3$, NHC(O)R6, CH$_2$OC(O)NR6R8, CH$_2$NR6R8, NHC(O)OR6, NHC(O)NR6R8, CH$_2$NHSO$_2$R6, CH$_2$NHC(O)R6, OC(O)R6, or NHC(O)R6, which may be substituted or unsubstituted;

Z is $C_{1-8}$ alkyl, CN, OH, or halogen;

m and p are independently 0-3;

Y is a bond, $C_{1-8}$ alkylene, —C(O)—, —C(O)O—, —CH(OH)—, or —C(O)NR10;

R5 is H, halogen, CN, lower alkyl, OH, OCH$_3$ or OCF$_3$;

Wherein R1 may be substituted by one or more of $C_{1-8}$ alkyl, a $C_{6-14}$ aryl group, $C_{1-8}$haloalkyl, $C_{1-8}$ alkoxy, halo, NH$_2$, CN, OCF$_3$, OH, C(O)NR6R8, C(O)R6, NR6R8, NHC(O)R6, SO$_2$R6, SO$_2$NR6R8;

R9 and R10 are independently $C_{1-8}$alkyl or H;

R6 and R8 are independently H, $C_{1-8}$alkyl, $C_{2-8}$ alkenyl, $C_{3-14}$ cycloalkyl, a $C_{6-14}$ aryl group, a 5-14 membered heteroaryl group, a 3-14 membered cycloheteroalkyl group, $C_{1-8}$haloalkyl, $C_{1-8}$ alkylOH, $C_{1-8}$alkoxy, or two R6 on one atom can form a heteroatom containing ring; and Wherein R4, R6, and R8 can be unsubstituted or substituted by one or more of $C_{1-8}$ alkyl, $C_{3-14}$ cycloalkyl, a $C_{6-14}$ aryl group, a 5-14 membered heteroaryl group, a 3-14 membered cycloheteroalkyl group, $C_{1-8}$ alkylOH, OH, oxo, $C_{1-8}$haloalkyl, carboxC$_{1-8}$ alkyl, or SO$_2$C$_{1-8}$alkyl, halo, —OCH$_3$, —OCF$_3$, —OH, —NH$_2$.

In another embodiment, the present invention includes compounds of Formula III wherein R7 is

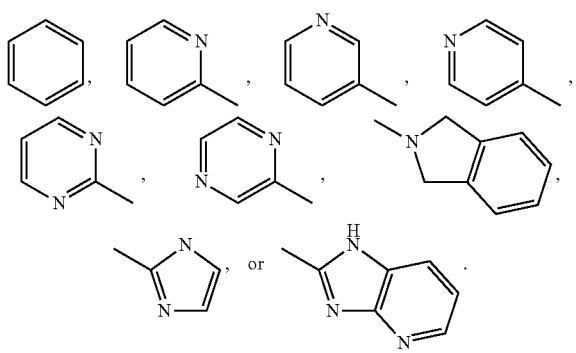

In another embodiment, the present invention includes compounds of Formula III according to claim 1 wherein R1 is

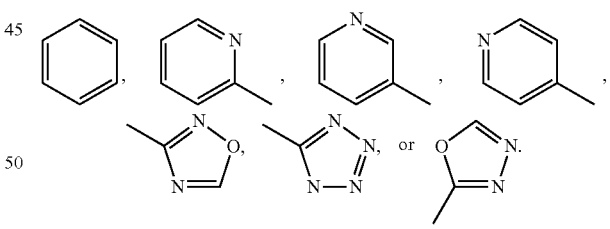

In another embodiment, the present invention includes compounds of Formula III wherein R7 is

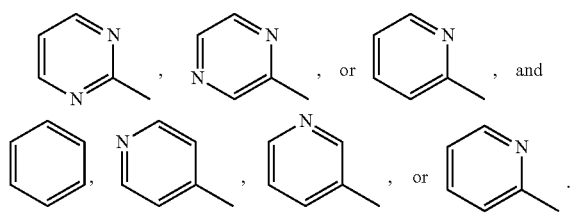

R1 is

In yet another embodiment, the present invention includes compounds of Formula III wherein R4 is $C(O)OC_{1-8}$ alkyl, $CF_3$, $C(O)R6$, $C(O)NR6R8$, $C_{1-8}$haloalkyl, $C_{1-8}$alkylOH, $C(O)R6$, $SO_2R6$, $C(O)NHC_{1-8}$alkylR6, $C(CH_3)(CH_3)(OH)$, $C(O)CH_3$, $C(CH_2)CH_3$, or $C(CH_3)(CH_2OH)OH$; and R6 and R8 are independently H, $C_{1-8}$alkyl, $C_{1-8}$ alkenyl, $C_{3-14}$ cycloalkyl, a $C_{6-14}$ aryl group, a 5-14 membered heteroaryl group, or a 3-14 membered cycloheteroalkyl group.

In another embodiment, the present invention includes compounds of Formula III wherein R4 is

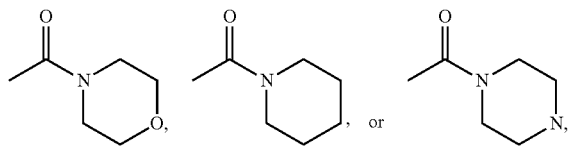

which may be unsubstituted or substituted.

In another embodiment, the present invention includes compounds of Formula III wherein R2 and R3 are $C_{1-8}$alkyl.

In a still further embodiment, the present invention includes compounds of Formula III wherein R2 and R3 are $CH_3$.

In another embodiment, the present invention includes compounds of Formula III wherein L is —O—, —NH—, —C(O)—, —CH(OH)—, —CH$_2$—, —CF$_2$—, —CHF—, —COH—, or a bond. In another embodiment, the present invention includes compounds of Formula III wherein L is —CH$_2$—. In another embodiment, the present invention includes compounds of Formula III wherein both X are N, and Z is $CH_3$.

In another embodiment, the present invention includes a compound of formula (IIIa):

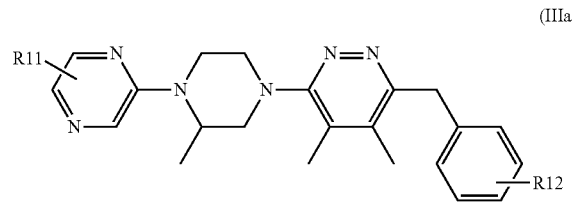

(IIIa)

and pharmaceutically acceptable salts thereof, wherein

R11 is $C_{1-8}$ alkyl, $C_{2-8}$ alkenyl, $C_{3-14}$ cycloalkyl, a $C_{6-14}$ aryl group, a 5-14 membered heteroaryl group, a 3-14 membered cycloheteroalkyl group, $C_{1-8}$alkoxy, halo, NR13R14, $C(O)OR13$, $C(O)NR13R14$, $C_{1-8}$haloalkyl, formyl, carbalkoxy, $C_{1-8}$alkylOH, $C(O)R13$, $SO_2R13$, $C(O)NHC_{1-8}$alkylR13, NR13R14, $SO_2NR13R14$, $OCF_3$, NHC(O)R13, $CH_2OC(O)NR13R14$, $CH_2NR13R14$, NHC(O)OR13, NHC(O)NR13R14, $CH_2NHSO_2R13$, $CH_2NHC(O)OR13$, OC(O)R13, or NHC(O)R13, which may be substituted or unsubstituted;

R12 is $C_{1-8}$ alkyl, a $C_{6-14}$ aryl group, $C_{1-8}$ haloalkyl, $C_{1-8}$alkoxy, halo, NH$_2$, CN, $OCF_3$, OH, $C(O)NR13R14$, $C(O)R13$, NR13R14, NHC(O)R13, $SO_2R13$, $SO_2NR13R14$;

R13 and R14 are independently H, $C_{1-8}$alkyl, $C_{2-8}$ alkenyl, $C_{3-14}$ cycloalkyl, a $C_{6-14}$ aryl group, a 5-14 membered heteroaryl group, a 3-14 membered cycloheteroalkyl group, $C_{1-8}$haloalkyl, $C_{1-8}$ alkylOH, $C_{1-8}$alkoxy, or R13 and R14 on one atom can form a heteroatom containing ring; and Wherein R11, R13, and R14 can be unsubstituted or substituted by one or more of $C_{1-8}$ alkyl, $C_{3-14}$ cycloalkyl, a $C_{6-14}$ aryl group, a 5-14 membered heteroaryl group, a 3-14 membered cycloheteroalkyl group, $C_{1-8}$ alkylOH, OH, oxo, $C_{1-8}$haloalkyl, carbox$C_{1-8}$alkyl, or $SO_2C_{1-8}$alkyl, halo, —OCH$_3$, —OCF$_3$, —OH, —NH$_2$.

Smoothened inhibitors can include the compounds described in PCT publication WO2003011219 (e.g., compound N-[4-Chloro-3-(5-dimethylamino-1H-benzoimidazol-2-yl)-phenyl]-3,5-dimethoxy-benzamide (referred to herein as Compound 2)), the contents of which are hereby incorporated by reference. Smoothened inhibitors can also include the compounds described in PCT publication WO2003011219, the contents of which are hereby incorporated by reference. Smoothened inhibitors can also include the compounds described in PCT publications WO2006028958 (e.g., compound 2-chloro-N-(4-chloro-3-(pyridin-2-yl)phenyl)-4-(methylsulfonyl)benzamide), WO200814291, WO07120827, and WO0650351, the contents of all of which are hereby incorporated by reference.

The methods of the present invention comprise use of a pharmaceutical compositions which contain Smoothened inhibitors, e.g., compounds of Formula I, Formula II, or Formula III, or any of the compounds listed herein or incorporated by reference, or a N-oxide derivative, individual isomers and mixture of isomers thereof; or a pharmaceutically acceptable salt thereof, in admixture with one or more suitable excipients.

Smoothened inhibitors utilized in the methods of the invention can be prepared as described in PCT patent publications WO01/05767 and WO00/05201, and in Ksander, et al. (2001) Journal of Medicinal Chemistry, 44:4677, the contents of all of which are herein incorporated by reference.

Compounds of Formula II and IIa are further described in the contents of U.S. patent application Ser. No. 12/503,565, which has counterpart International Application No. PCT/EP09/059,138.

A preferred compound of formula (II) is 2-[(R)-4-(6-Benzyl-4,5-dimethyl-pyridazin-3-yl)-2-methyl-3,4,5,6-tetrahydro-2H-[1,2]bipyrazinyl-5'-yl]-propan-2-ol, (also identified as Compound 3 in this document), of the below formula:

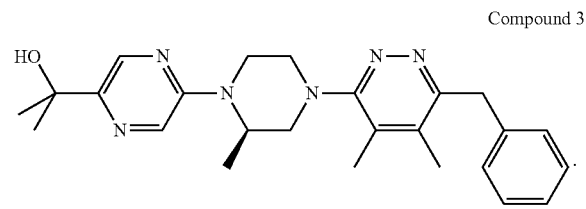 [SMILES: Cc1c(Cc2ccccc2)nnc(N2CCN(c3cnc(C(C)(C)O)cn3)[C@H](C)C2)c1C]

Compound 3

2-[(R)-4-(6-Benzyl-4,5-dimethyl-pyridazin-3-yl)-2-methyl-3,4,5,6-tetrahydro-2H-[1,2]bipyrazinyl-5'-yl]-propan-2-ol can be made according to Scheme 1:

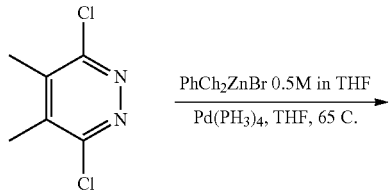

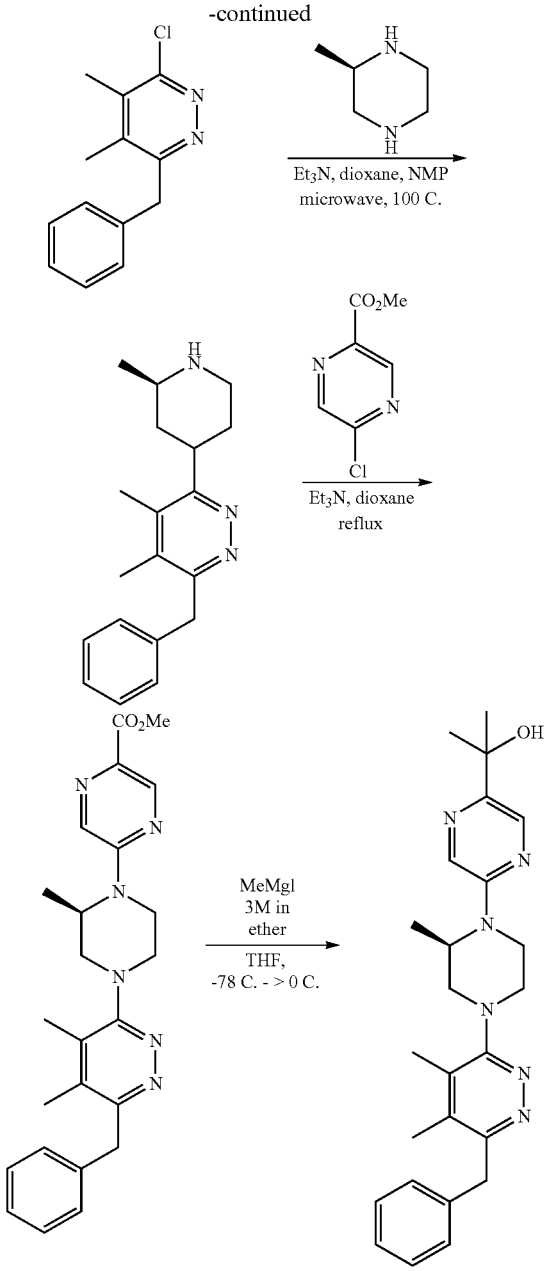

First step: A mixture of 4,5-dimethyl-1,4-dichloro-pyridazine (10 g, 56.5 mmol), tetrakis(triphenylphosphine)palladium(0) (3.3 g, 2.80 mmol) and THF (200 mL) is degassed and then benzylzinc bromide (147 mL, 0.5 M in THF, 73.40 mmol) is added. The reaction solution is heated to 65° C. overnight. Solvent is removed. Water is added and the water layer is extracted with EtOAc. The organic layer is concentrated to afford a crude product that is purified by chromatography on silica gel (EtOAc/Heptane: 0%~50%) to give 3-benzyl-6-chloro-4,5-dimethyl-pyridazine (9.5 g, 67%).

Second step: 3-Chloro-4,5-dimethyl-6-((R)-3-methyl-piperazin-1-yl)-pyridazine (400 mg, 1.66 mmol, 1 eq) is added to a solution of benzylzinc bromide (12.3 mL 0.5 M in THF, 6.64 mmol, 4 eq) and tetrakis(triphenylphosphine)palladium (100 mg, 0.08 mmol, 0.05 eq) in a microwave vial. The vial is sealed and irradiated in the microwave at 100° C. (high absorption setting) for 40 min. The reaction mixture is concentrated and purified by silica gel chromatography (5-20% EtOAc/heptane) to 3-benzyl-4,5-dimethyl-6-((R)-3-methyl-piperazin-1-yl)-pyridazine (324 mg, 66%).

Third step: A mixture of the above compound (6.0 g, 20.27 mmol), 5-chloropyrazine-2-carboxylic acid methyl ester (5.3 g, 30.30 mmol), Et₃N (6.2 g, 60.60 mmol) and dioxane (100 mL) is heated to reflux overnight. Solvent is removed. Saturated NH₄Cl solution is added and extracted with EtOAc. The organic layer is concentrated to afford the crude product that is purified by chromatography on silica gel (EtOAc/heptane: 50%~100%) to (R)-4-(6-benzyl-4,5-dimethyl-pyridazin-3-yl)-2-methyl-3,4,5,6-tetrahydro-2H-[1,2]bipyrazinyl-5'-carboxylic acid methyl ester (6.6 g, 76%) as a yellow solid.

Final step: To a solution of (R)-4-(6-benzyl-4,5-dimethyl-pyridazin-3-yl)-2-methyl-3,4,5,6-tetrahydro-2H-[1,2']bipyrazinyl-5'-carboxylic acid methyl ester (840 mg, 1.85 mmol) in THF (12 mL) is added methyl magnesium bromide (5 mL, 15 mmol, 3M in ether) at −78° C. The reaction mixture is stirred at 0° C. for 2 h then diluted with DCM and washed with NH₄Cl and water. The combined organic layers are washed with water, brine, dried over Na₂SO₄, filtered and concentrated down. Purification by HPLC of the crude product with acetonitrile in water (from 10% to 95% with 3% 1-propanol) at 220 nm wavelength detection provides the desired compound 3 (400 mg, 50%) next to small amounts of the corresponding methyl ketone. The solvents are removed with a lyophilizer to provide the products as white powders.

Phosphoinositide 3-kinase (PI3K) inhibitor compounds, as further defined herein, can include compounds of Formula A

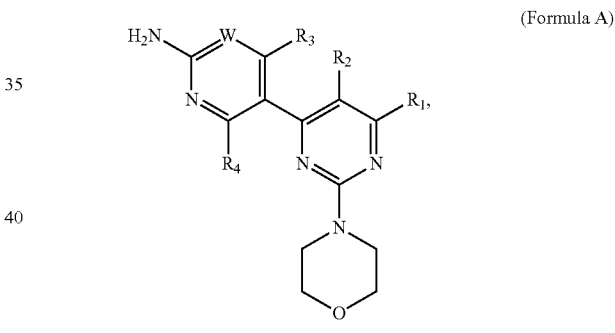

(Formula A)

or a stereoisomer, tautomer, or pharmaceutically acceptable salt thereof, wherein, W is CRw or N, wherein Rw is selected from the group consisting of W is $CR_w$ or N, wherein $R_w$ is selected from the group consisting
(1) hydrogen,
(2) cyano,
(3) halogen,
(4) methyl,
(5) trifluoromethyl,
(6) sulfonamido;
R1 is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,

(12) —COR1a,
(13) —CO2R1a,
(14) —CONR1aR1b,
(15) —NR1aR1b,
(16) —NR1aCOR1b,
(17) —NR1aSO2R1b,
(18) —OCOR1a,
(19) —OR1a,
(20) —SR1a,
(21) —SOR1a,
(22) —SO2R1a, and
(23) —SO2NR1aR1b,
wherein R1a, and R1b are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;
R2 is selected from the group consisting
(1) hydrogen,
(2) cyano,
(3) nitro,
(4) halogen,
(5) hydroxy,
(6) amino,
(7) substituted and unsubstituted alkyl,
(8) —COR2a, and
(9) —NR2aCOR2b,
wherein R2a, and R2b are independently selected from the group consisting of
(a) hydrogen, and
(b) substituted or unsubstituted alkyl;
R3 is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —COR3a,
(13) —NR3aR3b,
(14) —NR3aCOR3b,
(15) —NR3aSO2R3b,
(16) —OR3a,
(17) —SR3a,
(18) —SOR3a,
(19) —SO2R3a, and
(20) —SO2NR3aR3b,
wherein R3a, and R3b are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and
R4 is selected from the group consisting of
(1) hydrogen, and
(2) halogen.

The radicals and symbols as used in the definition of a compound of formula I have the meanings as disclosed in PCT publication WO07/084,786, which is hereby incorporated by reference. WO07/084,786 describes pyrimidine derivatives, which have been found to modulate the activity of lipid kinases, such as PI3-kinases. Specific pyrimidine derivatives which are suitable for the present invention, their preparation and suitable pharmaceutical formulations containing the same are described in WO07/084,786.

A preferred compound of the present invention is 5-(2,6-di-morpholin-4-yl-pyrimidin-4-yl)-4-trifluoromethyl-pyridin-2-ylamine (referred to herein as Compound A), the synthesis which is described in WO07/084,786 as Example 10.

Phosphatidylinositol 3-kinase (PI3K) inhibitor compounds, as further defined herein, can also include compounds of Formula B

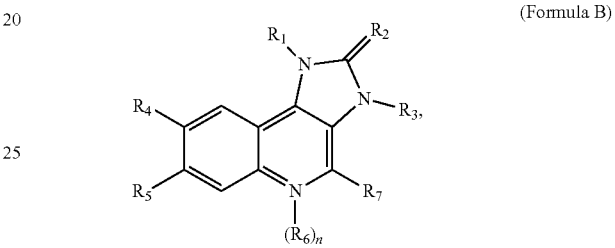

(Formula B)

wherein
$R_1$ is naphthyl or phenyl wherein said phenyl is substituted by one or two substituents independently selected from the group consisting of
Halogen;
lower alkyl unsubstituted or substituted by halogen, cyano, imidazolyl or triazolyl;
cycloalkyl;
amino substituted by one or two substituents independently selected from the group consisting of lower alkyl, lower alkyl sulfonyl, lower alkoxy and lower alkoxy lower alkylamino;
piperazinyl unsubstituted or substituted by one or two substituents independently selected from the group consisting of lower alkyl and lower alkyl sulfonyl;
2-oxo-pyrrolidinyl;
lower alkoxy lower alkyl;
imidazolyl;
pyrazolyl;
and triazolyl;
$R_2$ is O or S;
$R_3$ is lower alkyl;
$R_4$ is pyridyl unsubstituted or substituted by halogen, cyano, lower alkyl, lower alkoxy or piperazinyl unsubstituted or substituted by lower alkyl;
pyrimidinyl unsubstituted or substituted by lower alkoxy;
quinolinyl unsubstituted or substituted by halogen;
quinoxalinyl;
or phenyl substituted with alkoxy
$R_5$ is hydrogen or halogen;
n is 0 or 1;
$R_6$ is oxido;
with the proviso that if n=1, the N-atom bearing the radical $R_6$ has a positive charge;
$R_7$ is hydrogen or amino;
or a tautomer thereof, or a pharmaceutically acceptable salt, or a hydrate or solvate thereof.

Compounds B and C, referred to herein, are compounds of Formula B.

The methods and combinations of the present invention comprise use of a pharmaceutical compositions which contain Smoothened inhibitors, e.g., compounds of Formula I, Formula II, or Formula III, or any of the compounds listed herein or incorporated by reference, or a N-oxide derivative, individual isomers and mixture of isomers thereof; or a pharmaceutically acceptable salt thereof, in admixture with one or more suitable excipients.

PI3K inhibitors can include the compounds described in PCT publication WO2006/122806 (e.g., compound 2-methyl-2-[4-(3-methyl-2-oxo-8-quinolin-3-yl-2,3-dihydro-imidazo[4,5-c]quinolin-1-yl)-phenyl]-propionitrile (Compound B); and e.g., compound 8-(6-methoxy-pyridin-3-yl)-3-methyl-1-(4-piperazin-1-yl-3-trifluoromethyl-phenyl)-1,3-dihydro-imidazo[4,5-c]quinolin-2-one) (Compound C), the contents of which are hereby incorporated by reference. PI3K inhibitors can also include the compounds described in PCT publication WO07084786 (e.g., compound 5-(2,6-di-morpholin-4-yl-pyrimidin-4-yl)-4-trifluoromethyl-pyridin-2-ylamine, Compound A), the contents of which are hereby incorporated by reference.

PI3K inhibitors can also include the compounds described in PCT publications WO0712775, WO07129005, WO07129048, WO07129052, WO07129161, WO0713271, WO07122410, WO07080382, WO07087395, U.S. Ser. No. 07/238,730, US072387646, and WO07082956, the contents of which are hereby incorporated by reference.

PI3K inhibitors can also include inhibitors such as XL-147 and XL-765 (Exelixis™), as well as SF-1126 (Semaphore Pharmaceuticals™), PX-866 (Oncothyreon), and GDC0941 (Roche).

Definitions

Unless defined otherwise, all technical and scientific terms used herein have the same meaning as commonly understood by those of ordinary skill in the art to which this invention pertains. The following references provide one of skill with a general definition of many of the terms used in this invention: *Oxford Dictionary of Biochemistry and Molecular Biology*, Smith et al. (eds.), Oxford University Press (revised ed., 2000); *Dictionary of Microbiology and Molecular Biology*, Singleton et al. (Eds.), John Wiley & Sons ($3P^{rdP}$ ed., 2002); and *A Dictionary of Biology* (Oxford Paperback Reference), Martin and Hine (Eds.), Oxford University Press (4th ed., 2000). In addition, the following definitions are provided to assist the reader in the practice of the invention.

By "suppress and/or reverse," e.g., a Hedgehog-related disorder (e.g., cancer), Applicants mean to abrogate said Hedgehog-related disorder (e.g., cancer), or to render said condition less severe than before or without the treatment.

"Cure" as used herein means to lead to the remission of the Hedgehog-related disorder (e.g., cancer) in a patient, or of ongoing episodes thereof, through treatment.

The terms "prophylaxis" or "prevention" means impeding the onset or recurrence of a Hedgehog-related disorder (e.g., cancer).

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

"Subject" or "patient" refers to a mammal, preferably a human, in need of treatment for a condition, disorder or disease.

"Delay of progression" as used herein means that the administration of a Smoothened inhibitors (e.g., a compound of Formula I, Formula II, or Formula III, or any of the compounds listed herein or incorporated by reference) to patients in a pre-stage or in an early phase of a Hedgehog-related disorder (e.g., cancer) prevents the disease from evolving further, or slows down the evolution of the disease in comparison to the evolution of the disease without administration of the active compound.

The term "Combinations of the invention," or like phrases, refers to antagonists or inhibitors of the Smo signaling pathway (e.g., Smoothened inhibitors) in combination with one or more of the following: (i) cholesterol biosynthesis pathway inhibitors (e.g., statins); and (ii) Gli inhibitors.

The term "Hedgehog" is used to refer generically to any member of the Hedgehog family, including sonic, indian, desert and tiggy winkle. The term may be used to indicate protein or gene. The term is also used to describe homolog/ortholog sequences in different animal species.

The terms "Hedgehog (Hh) signaling pathway" and "Hedgehog (Hh) signaling" are used interchangeably and refer to the chain of events normally mediated by various members of the signaling cascade such as Hedgehog, patched (Ptch), smoothened (Smo), and Gli. The Hedgehog pathway can be activated even in the absence of a Hedgehog protein by activating a downstream component. For example, overexpression of Smo will activate the pathway in the absence of Hedgehog.

Hh signaling components or members of Hh signaling pathway refer to gene products that participate in the Hh signaling pathway. An Hh signaling component frequently materially or substantially affects the transmission of the Hh signal in cells/tissues, typically resulting in changes in degree of downstream gene expression level and/or phenotypic changes. Hh signaling components, depending on their biological function and effects on the final outcome of the downstream gene activation/expression, may be divided into positive and negative regulators. A positive regulator is an Hh signaling component that positively affects the transmission of the Hh signal, i.e., stimulates downstream biological events when Hh is present. Examples include Hedgehog, Smo, and Gli. A negative regulator is an Hh signaling component that negatively affects the transmission of the Hh signal, i.e., inhibits downstream biological events when Hh is present. Examples include (but are not limited to) Ptch and SuFu.

"Hedgehog gain-of-function" refers to an aberrant modification or mutation of a Ptc, Hedgehog, or Smo gene or protein, or a decrease (or loss) in the level of expression of such a gene, which results in a phenotype which resembles contacting a cell with a Hedgehog protein, e.g., aberrant activation of a Hedgehog pathway. "Hedgehog gain-of-function" can also refer to aberrant activation of a Hedgehog pathway resulting from an increase in expression of Hedgehog pathway natural ligands, and/or an increase in expression of Smo. The gain-of-function may include a loss of the ability of the Ptch gene product to regulate the level of expression of Gli genes, e.g., Gli1, Gli2, and Gli3. The term "Hedgehog gain-of-function" is also used herein to refer to any similar cellular phenotype (e.g., exhibiting excess proliferation) which occurs due to an alteration anywhere in the Hedgehog signal transduction pathway, including, but not limited to, a modification or mutation of Hedgehog itself. For example, a tumor cell with an abnormally high proliferation rate due to activation of the Hedgehog signaling pathway would have a "Hedgehog gain-of-function" phenotype, even if Hedgehog is not mutated in that cell.

"Patched loss-of-function" refers to an aberrant modification, amplification, or mutation of a Ptch gene or protein, or a decreased level of expression of the gene, which results in a phenotype which resembles contacting a cell with a Hedgehog protein, e.g., aberrant activation of a Hedgehog pathway. The loss-of-function may include a loss of the ability of the Ptch gene product to regulate the level of expression of Gli genes, e.g., Gli1, Gli2 and Gli3.

"Gli gain-of-function" refers to an aberrant modification, amplification, or mutation of a Gli gene or protein, or an increased level of expression of the gene, which results in a phenotype which resembles contacting a cell with a Hedgehog protein, e.g., aberrant activation of a Hedgehog pathway.

The term "inhibiting" or "inhibition," in the context of tumor growth or tumor cell growth, refers to delayed appearance of primary or secondary tumors, slowed development of primary or secondary tumors, decreased occurrence of primary or secondary tumors, slowed or decreased severity of secondary effects of disease, or arrested tumor growth and regression of tumors. The term "prevent" or "prevention" refers to a complete inhibition of development of primary or secondary tumors or any secondary effects of disease. In the context of reversible modulation of enzymatic activities, inhibition relates to reversible suppression or reduction of an enzymatic activity including competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex.

"Smoothened gain-of-function" refers to an aberrant modification or mutation of a Smo gene, or an increased level of expression of the gene, which results in a phenotype which resembles contacting a cell with a Hedgehog protein, e.g., aberrant activation of a Hedgehog pathway.

"Smoothened inhibitor" (or "Smoothened antagonists" or like phrases) as used herein describes agents capable of inhibiting, antagonizing, or arresting Smoothened, thereby inhibiting, antagonizing, or arresting Hedgehog pathway signaling. Smoothened inhibitors include but are not limited to cyclopamine, jervine, compounds of Formula I (e.g., a compound of Formulae (Ia), (Ib) or (Ic)), compounds of Formula II, compounds of Formula III, any of the anti-smoothened compounds individually listed herein, anti-Smo antibodies, and anti-Smo inhibitory nucleic acids (e.g., anti-Smo siRNAs). Smoothened inhibitors also include other known anti-Smoothened agents in the art and/or incorporated herein by reference.

"PI3K inhibitor" as used herein describes agents capable of inhibiting, antagonizing, or arresting PI3K-related biological activity and downstream effectors, e.g., activation of the PI3K pathway. For purposes of the present application, PI3K inhibitors can also include agents which inhibit downstream targets of PI3Ks, such as PDK1, Akt and mTOR (mammalian target of rapamycin).

PI3K inhibitors can include the compounds listed herein as part of Formula A and B. PI3K inhibitors can also include lipid kinase inhibitors and inhibitory nucleotides against PI3K such as siRNAs. PI3K inhibitors can also include compounds described in PCT publication WO2006/122806 (e.g., compound 2-methyl-2-[4-(3-methyl-2-oxo-8-quinolin-3-yl-2,3-dihydro-imidazo[4,5-c]quinolin-1-yl)-phenyl]-propionitrile, Compound B; and e.g., compound 8-(6-methoxy-pyridin-3-yl)-3-methyl-1-(4-piperazin-1-yl-3-trifluoromethyl-phenyl)-1,3-dihydro-imidazo[4,5-c]quinolin-2-one), Compound C, the contents of which are hereby incorporated by reference. PI3K inhibitors can also include the compounds described in PCT publication WO07084786 (e.g., compound 5-(2,6-di-morpholin-4-yl-pyrimidin-4-yl)-4-trifluoromethyl-pyridin-2-ylamine, Compound A), the contents of which are hereby incorporated by reference.

PI3K inhibitors can also include the compounds described in PCT publications WO0712775, WO07129005, WO07129048, WO07129052, WO07129161, WO0713271, WO07122410, WO07080382, WO07087395, U.S. Ser. No. 07/238,730, US072387646, and WO07082956, the contents of which are hereby incorporated by reference.

PI3K inhibitors can also include inhibitors such as XL-147 and XL-765 (Exelixis™), as well as SF-1126 (Semaphore Pharmaceuticals™), PX-866 (Oncothyreon), and GDC0941 (Roche).

"Gli inhibitor" as used herein describes agents capable of inhibiting, antagonizing, or arresting Gli-related activity, e.g., gene transactivation. Gli inhibitors include agents which are capable of inhibiting Hedgehog pathway-related activity (e.g., aberrant activity which results in Hedgehog-related disorders) associated with activation downstream of Smoothened. Non-limiting examples of Gli inhibitors include GANT61 (Gli-ANTagonist 61), GANT58, zerumbone, zerumbone epoxide, staurosporinone, 6-hydroxystaurosporinone, arcyriaflavin C, 5,6-dihydroxyarcyriaflavin A, and physalins F and B.

In the present description, the term "treatment" may include both prophylactic or preventive treatment as well as curative or disease suppressive treatment, including treatment of patients at risk for a disorder of the invention (e.g., a Hedgehog-related disorder (e.g., cancer)) as well as ill patients. This term further includes the treatment for the delay of progression of the disease.

"Treatment" or "treating" includes the administration of compounds or agents to prevent or delay the onset of the symptoms, complications, or biochemical indicia of a disease (e.g., leukemia), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The term "treat" or "treatment" also refers to arrested tumor growth, and to partial or complete regression of tumors, and includes the administration of compounds or agents to prevent or delay the onset of the symptoms, complications, or biochemical indicia of a disease (e.g., cancer), alleviating the symptoms or arresting or inhibiting further development of the disease, condition, or disorder.

As used herein a "small organic molecule" is an organic compound (or organic compound complexed with an inorganic compound (e.g., metal)) that has a molecular weight of less than 3 kilodaltons, and preferably less than 1.5 kilodaltons.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

"Analog" as used herein, refers to a small organic compound, a nucleotide, a protein, or a polypeptide that possesses similar or identical activity or function(s) as the compound, nucleotide, protein or polypeptide or compound having the desired activity and therapeutic effect of the present invention. (e.g., inhibition of tumor growth), but need not necessarily comprise a sequence or structure that is similar or identical to the sequence or structure of the preferred embodiment "Apoptosis" refers to programmed cell death and is characterized by certain cellular characteristics such as membrane blebbing, chromatin condensation and fragmentation, formation of apoptotic bodies and a positive "TUNEL" staining pattern. Degradation of genomic DNA during apoptosis results in formation of characteristic, nucleosome sized DNA fragments; this degradation produces a diagnostic (about) 180 bp laddering pattern when analyzed by gel electrophoresis. A later step in the apoptotic process is degradation of the plasma membrane, rendering apoptotic cells leaky to various dyes (e.g., trypan blue and propidium iodide).

"Derivative" refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

"Inhibitors," or "antagonists" refer to inhibitory molecules identified using in vitro and in vivo assays for Hh pathway function, e.g., Smo antagonists. In particular, inhibitors and antagonists refer to compounds or agents that decrease signaling that occurs via the Hh pathway. Inhibitors may be compounds that decrease, block, or prevent, signaling via this pathway.

"Hedgehog-related disorder(s)" as used herein includes disorders associated with disruption or aberrance of the Hedgehog pathway, as well as disorders associated with normal but undesired growth states relating to activation of the Hedgehog pathway. "Hedgehog-related disorder(s)" include but are not limited to tumor formation, cancer, neoplasia, malignant hyperproliferative disorders, and non-malignant hyperproliferative disorders. "Hedgehog-related disorder(s)" also include benign prostate hyperplasia, psoriasis, wet macular degeneration, osteopetrosis and unwanted hair growth.

As used herein, the term "cancer" includes solid mammalian tumors as well as hematological malignancies. "Solid mammalian tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin, central nervous system including brain; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Information regarding numerous types of cancer can be found, e.g., from the American Cancer Society, or from, e.g., Wilson et al. (1991) Harrison's Principles of Internal Medicine, 12th Edition, McGraw-Hill, Inc. Both human and veterinary uses are contemplated.

Cancers which are particularly amenable to treatment by the methods of the invention include but are not limited to gliomas, medulloblastomas (e.g., cerebellar medulloblastomas), pericytoma, primitive neuroectodermal tumors (PNETS), basal cell carcinoma (BCC), small cell lung cancers, large cell lung cancers, tumors of the gastrointestinal tract, rhabdomyo sarcomas, breast cancer, soft tissue sarcomas, pancreatic tumors, bladder tumors and prostate tumors.

As used herein, "sensitive tumors" means tumors (e.g., medulloblastomas) which, due to hedgehog pathway activation, respond to treatment with a smoothened inhibitor anti-cancer regimen.

As used herein, "resistant tumors" means formerly sensitive tumors (e.g., medulloblastomas) which, in the continous presence of a smo inhibitor, either have regrown after shrinking due to treatment, or have reappeared after being temporarily eliminated due to treatment. Resistant tumors show a decreased sensitivity or no response to smoothened inhibition. Successful treatment of resistant tumors can engender, e.g., increased sensitivity of a tumor cell to novel or previously attempted anti-cancer regimen and/or chemotherapeutic agents, and can result in, e.g., subsequent tumor cell death and prevention from metastasis.

As used herein, "statin" means any of a class of drugs that inhibit a key enzyme involved in the synthesis of cholesterol and promote receptor binding of LDL-cholesterol, resulting in decreased levels of serum cholesterol and LDL-cholesterol and increased levels of HDL-cholesterol. These are often referred to as a subset of sterol synthetic pathway inhibitors (SSPIs), and reduce serum cholesterol levels by inhibiting HMG-CoA reductase, a key enzyme involved in the biosynthesis of cholesterol. Statins include pravastatin, simvastatin, lovastatin, fluvastatin, atorvastatin, cerivastatin, rosuvastatin, and pitavastatin.

As used herein, the term "malignant hyperproliferative disorder(s)" includes but is not limited to cancers, neuronal proliferative disorders, bone marrow proliferative diseases and leukemias.

As used herein, the term "non-malignant hyperproliferative disorder(s)" includes but is not limited to non-malignant and non-neoplastic proliferative disorders, such as smooth muscle hyperplasia in blood vessels, cutaneous scarring, and pulmonary fibrosis.

As used herein, "cholesterol biosynthesis pathway inhibitor" means agents which are capable of inhibiting or arresting the generation or synthesis of cholesterol, which, for example, begins in the cytoplasm and microsomes with the conversion of the two-carbon acetate group of acetyl-CoA. Cholesterol biosynthesis is strictly regulated in order to prevent over-accumulation and abnormal deposition of cholesterol within the body (which can, inter alia, lead to cardiovascular disease). Inhibitors of this pathway include the class of sterol synthetic pathway inhibitors (SSPIs), which includes but is not limited to, (i) statins; (ii) zaragozic acid A (ZGA), a squalene synthesis inhibitor that blocks conversion of isoprenoids into sterols, leaving only isoprenoid synthesis intact; ketoconazole, which allows synthesis of an early sterol, lanosterol, but prevents synthesis of downstream sterols; (iv) triparanol (TPL), which blocks the final step of cholesterol synthesis, allowing production of sterols other than cholesterol and its derivatives; and (v) aminoglutethimide, which blocks conversion of cholesterol to pregnenelone and other steroids, leaving sterol synthesis unaffected.

The term "alkyl" refers to straight or branched chain hydrocarbon groups having 1 to 20 carbon atoms, preferably lower alkyl of 1 to 7 carbon atoms. Exemplary alkyl groups include methyl, ethyl, propyl, isopropyl, n-butyl, t-butyl, isobutyl, pentyl, hexyl, isohexyl, heptyl, 4,4-dimethylpentyl, octyl and the like. Preferred is $C_1$-$C_4$-alkyl.

The term "lower" referred to herein in connection with organic radicals or compounds respectively generally defines, if not defined differently, such with up to and including 7, preferably up and including 4 and advantageously one or two carbon atoms. Such may be straight chain or branched.

The term "optionally substituted alkyl" refers to unsubstituted or substituted straight or branched chain hydrocarbon groups having 1 to 20 carbon atoms, preferably lower alkyl of 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like.

The term "substituted alkyl" refers to alkyl groups substituted by one or more of the following groups: halo (such as F, Cl, Br and I), hydroxy, alkoxy, alkoxyalkoxy, aryloxy, cycloalkyl, alkanoyl, alkanoyloxy, amino, substituted amino, alkanoylamino, thiol, alkylthio, arylthio, alkylthiono, alkylsulfonyl, arylsulfonyl, heteroarylsulfonyl, amino sulfonyl, nitro, cyano, carboxy, carbamyl, alkoxycarbonyl, aryl, aralkoxy, guanidino, heterocyclyl (e.g., indolyl, imidazolyl, furyl, thienyl, thiazolyl, pyrrolidyl, pyridyl, pyrimidyl), and the like.

The term "halogen" or "halo" refers to fluorine, chlorine, bromine and iodine.

The term "alkoxy" or "alkyloxy" refers to alkyl-O—.

The term "aryl" or "ar", refers to carbocyclic monocyclic or bicyclic aromatic hydrocarbon groups having 6 to 12 carbon atoms in the ring portion, such as phenyl, naphthyl, tetrahydronaphthyl, and biphenyl groups, each of which may optionally be substituted by one to four, e.g., one or two, substituents such as alkyl, halo, trifluoromethyl, hydroxy, alkoxy, alkanoyl, alkanoyloxy, amino, substituted amino, alkanoylamino, thiol, alkylthio, nitro, cyano, carboxy, carboxyalkyl, carbamyl, alkoxycarbonyl, alkylthiono, alkylsulfonyl, aminosulfonyl, and the like. "Arylene" means a divalent radical derived from an aryl group.

The term "aralkyl" refers to an aryl group linked to an alkyl group, such as benzyl.

The term "haloalkyl" refers to alkyl which mono- or polysubstituted by halo, such as trifluoromethoxy.

The term "alkylene" refers to a straight chain bridge of 1 to 6 carbon atoms connected by single bonds (e.g., —(CH2)$_x$— wherein x is 1 to 6) which may be substituted with 1 to 3 lower alkyl groups.

The term "alkylene interrupted by O, S, N—(H, alkyl or aralkyl)" refers to a straight chain of 2 to 6 carbon atoms which is interrupted by O, S, N—(H, alkyl or aralkyl), such as (m)ethyleneoxy(m)ethylene, (m)ethylenethio(m)ethylene, or (m)ethyleneimino(m)ethylene.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

The term "alkanoyloxy" refers to alkyl-C(O)—O—.

The terms "alkylamino" and "dialkylamino" refer to (alkyl)NH— and (alkyl)$_2$N—, respectively.

The term "alkanoylamino" refers to alkyl-C(O)—NH—.

The term "alkylthio" refers to alkyl-S—.

The term "alkylthiono" refers to alkyl-S(O)—.

The term "alkylsulfonyl" refers to alkyl-S(O)$_2$—

The term "carbamyl" refers to —C(O)-amino or —C(O)-substituted amino.

The term "alkoxycarbonyl" refers to alkyl-O—C(O)—.

The term "acyl" refers to alkanoyl, aroyl, heteroaryol, arylalkanoyl, heteroarylalkanoyl, and the like.

The term "heteroaryl" or "heteroar" refers to an aromatic heterocycle, for example monocyclic or bicyclic heterocyclic aryl, such as pyrrolyl, pyrazolyl, imidazolyl, oxazolyl, thiazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by one to four, e.g. one or two, substituents, such as lower alkyl, lower alkoxy or halo, the point of attachment of said heterocycle being at a carbon atom of the heterocyclic ring. Preferred heteroaryl residues are 1-methyl-2-pyrrolyl, 2-, 3-thienyl, 2-thiazolyl, 2-imidazolyl, 1-methyl-2-imidazolyl, 2-,3-,4-pyridyl, or 2-quinolyl.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe combinations of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

The term "alkanoyl" refers, for example, to $C_2$-$C_7$-alkanoyl, especially $C_2$-$C_5$-alkanoyl, such as acetyl, propionyl or pivaloyl.

The term "aralkoxy" refers to an aryl group linked to an alkoxy group.

The term "arylsulfonyl" refers to aryl-SO$_2$—.

The term "aroyl" refers to aryl-CO—.

The term "heterocyclyl" refers to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazoliclinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, enzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl) and the like.

Exemplary tricyclic heterocyclic groups include carbazolyl, benzidolyl, phenanthrolinyl, acridinyl, phenanthridinyl, xanthenyl and the like.

The term "heterocyclyl" also includes substituted heterocyclic groups. Substituted heterocyclic groups refer to heterocyclic groups substituted with 1, 2 or 3 of the following:
(a) alkyl;
(b) hydroxy (or protected hydroxy);
(c) halo;
(d) oxo (i.e. =O);
(e) amino or substituted amino;
(f) alkoxy;
(g) cycloalkyl;
(h) carboxy;
(i) heterocyclooxy;
(j) alkoxycarbonyl, such as unsubstituted lower alkoxycarbonyl;
(k) carbamyl, alkylcarbamyl, arylcarbamyl, dialkylcarbamyl;
(l) mercapto;
(m) nitro;
(n) cyano;
(o) sulfonamido, sulfonamidoalkyl or sulfonamidodialkyl;
(p) aryl;
(q) alkylcarbonyloxy;
(r) arylcarbonyloxy;
(s) arylthio;
(t) aryloxy;
(u) alkylthio;
(v) formyl;
(w) arylalkyl; or
(x) aryl substituted with alkyl, cycloalkyl, alkoxy, hydroxy, amino, alkylamino, dialkylamino or halo.

The term "heterocyclooxy" denotes a heterocyclic group bonded through an oxygen bridge.

The term "heteroarylsulfonyl" refers to heteroaryl-$SO_2$—
The term "heteroaroyl" refers to heteroaryl-CO—.

The term "acylamino" refer to acyl-NH—.

The term "substituted amino" refers to amino mono- or, independently, disubstituted by alkyl, aralkyl, aryl, heteroaryl, cycloalkyl, cycloalkylalkyl, heteroaralkyl, or disubstituted by lower alkylene or lower alkylene interrupted by O, S, N—(H, alkyl, aralkyl) and the like.

As used herein, "contacting" has its normal meaning and refers to combining two or more molecules (e.g., a small molecule organic compound and a polypeptide) or combining molecules and cells (e.g., a compound and a cell). Contacting can occur in vitro, e.g., combining two or more agents or combining a compound and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

Pharmaceutically acceptable salts of any acidic Smoothened inhibitor compounds used with the methods of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly, acid addition salts, such as of mineral acids, organic carboxylic, and organic sulfonic acids e.g., hydrochloric acid, methanesulfonic acid, maleic acid, are possible provided a basic group, such as amino or pyridyl, constitutes part of the structure.

Pharmaceutically acceptable salts of the Smoothened inhibitor compounds used with the methods of the invention are particularly acid addition salts, such as of mineral acids, organic carboxylic, and organic sulfonic acids e.g., hydrochloric acid, methanesulfonic acid, maleic acid, and the like provided a basic group, such as pyridyl, constitutes part of the structure.

The Smoothened inhibitor compounds used with the methods of the invention, depending on the nature of the substituents, possess one or more asymmetric carbon atoms, and therefore exist as racemates and the (R) and (S) enantiomers thereof. Preferred is the more active enantiomer typically assigned the S-configuration (at the carbon being the $NR_6R_7$ substituent).

The present invention relates to the discovery that signal transduction pathways regulated by Hh and/or Smo can be modulated by a combination of Smoothened inhibitors (e.g., cyclopamine, jervine, compounds of Formula I (e.g., a compound of Formulae (Ia), (Ib) or (Ic)), compounds of Formula II, compounds of Formula III, any of the anti-smoothened compounds individually listed herein, anti-Smo antibodies, and anti-Smo inhibitory nucleic acids (e.g., anti-Smo siRNAs)) and cholesterol biosynthesis pathway inhibitors (e.g., statins), Gli inhibitors, and/or Phosphatidylinositol 3-kinase (PI3K) inhibitors. Said modulation can occur when the Hh/Smo pathway is active despite having been previously subjected to a Smoothened antagonist (e.g., as is the case with resistant tumors). Said modulation can also occur with when the Hh/Smo pathway is active despite not having been previously subjected to a Smoothened antagonist (e.g., as is the case with sensitive tumors).

The present invention relates generally to the diagnosis and treatment of pathologies relating to the Hedgehog pathway (defined below and referred to herein as "Hedgehog-related disorder(s)"), including but not limited to tumor formation, cancer, neoplasia, and non-malignant hyperproliferative disorders, and more particularly to methods of inhibiting tumorigenesis, tumor growth and tumor survival using agents known to inhibit the Hedgehog and Smo signaling pathway, e.g., Smoothened inhibitors in combination with one or more of the following: (i) cholesterol biosynthesis pathway inhibitors (e.g., statins); (ii) Gli inhibitors; and/or (iii) Phosphatidylinositol 3-kinase (PI3K) inhibitors. Smoothened inhibitors is a class defined herein and includes, but is not limited to, anti-Smoothened antibodies or inhibitory nucleotides (e.g., RNAi), compounds of Formula I, Formula II, or Formula III, or any of the compounds listed herein or incorporated by reference, and other known anti-Smoothened agents in the art and/or incorporated herein by reference. Phosphatidylinositol 3-kinase (PI3K) inhibitors is also a class defined herein and includes, but is not limited to, compounds of Formula A, as well as lipid kinase inhibitors and anti-PI3K inhibitory nucleotides (e.g., RNAi).

The methods and compounds of the present invention relate to inhibiting activation of the Hedgehog signaling pathway, e.g., by inhibiting aberrant growth states resulting from phenotypes such as Ptch loss-of-function, Hedgehog gain-of-function, Smoothened gain-of-function or Gli gain-of-function, and comprise contacting the cell with a combination of agents known to inhibit the Hedgehog and Smo signaling pathway, e.g., Smoothened inhibitors, and cholesterol biosynthesis inhibitors (e.g., statins); Gli inhibitors; and/or Phosphatidylinositol 3-kinase (PI3K) inhibitors in a sufficient amount to agonize a normal Ptch activity, antagonize a normal Hedgehog activity, or antagonize smoothened activity (e.g., to reverse or control the aberrant growth state).

One aspect of the present invention includes methods employing compounds for inhibiting Smo-dependent pathway activation (e.g., when Smo is activated by the presence of the Hedgehog ligand). Another aspect of the present invention includes methods employing compounds for inhibiting Hedgehog (ligand)-independent pathway activation. In certain embodiments, the present methods can be used to counteract the phenotypic effects of unwanted activation of a Hedgehog pathway, such as resulting from Hedgehog gain-of-function, Ptch loss-of-function or smoothened gain-of-function mutations, whether the activation is in the presence or absence of the Hedgehog ligand. For instance, a method of the invention can involve contacting a cell (in vitro or in vivo) with a Smo antagonist, such as a Smoothened inhibitor, in combination with cholesterol biosynthesis pathway inhibitors (e.g., statins), Gli inhibitors, and/or Phosphatidylinositol 3-kinase (PI3K) inhibitors, in an amount sufficient to antagonize smoothened-dependent or smoothened-independent (i.e., if activation occurs downstream of smoothened) Hedgehog pathway signaling, in the presence or absence of the Hedgehog ligand.

Certain embodiments of the present invention provide methods for inhibiting the synthesis, expression, production, stabilization, phosphorylation, relocation within the cell, and/or activity of a Smo protein in a cell in vitro or in vivo, comprising contacting said cell with, or introducing into said cell, a combination of Smoothened inhibitors and cholesterol biosynthesis pathway inhibitors (e.g., statins), Gli inhibitors, and/or Phosphatidylinositol 3-kinase (PI3K) inhibitors. In certain embodiments, proteins downstream of Smo in the Hedgehog signaling pathway (e.g., Gli) are also inhibited in a cell in vitro or in vivo. For example, the synthesis, expression, production, stabilization, phosphorylation, relocation within the cell, and/or activity of Gli protein(s) may be inhibited, in addition to the inhibition of Smoothened as described above, comprising contacting said cell with, or introducing into said cell, a combination of Smoothened inhibitors and cholesterol biosynthesis pathway inhibitors (e.g., statins), Gli inhibitors, and/or Phosphatidylinositol 3-kinase (PI3K) inhibitors. In certain embodiments, said Smo protein is active despite having been previously subjected to a Smoothened antagonist (e.g., as is the case with resistant tumors). In other embodiments, said Smo protein has not been previously subjected to a Smoothened antagonist.

The methods of the present invention may be used to regulate proliferation and/or differentiation of cells in vitro and/or in vivo, e.g., in the formation of tissue from stem cells, or to prevent the growth of hyperproliferative cells. In another particular embodiment, contacting the cell with—or introducing into the cell—a combination of Smoothened inhibitors and cholesterol biosynthesis pathway inhibitors (e.g., statins), Gli inhibitors, and/or Phosphatidylinositol 3-kinase (PI3K) inhibitors results in inhibition of cellular proliferation, inhibition of tumor cell growth and/or survival, and/or inhibition of tumorigenesis. Thus, another particular embodiment provides methods for inhibiting and/or antagonizing the Hh pathway by employing combination methods of the invention in tumor cells. In certain embodiments, said cellular proliferation, tumor cell growth and/or survival, and/or tumorigenesis is associated with resistant tumors. In other embodiments, said cellular proliferation, tumor cell growth and/or survival, and/or tumorigenesis is associated with sensitive tumors.

The combinations of the invention may be administered in certain embodiments to a patient afflicted by sensitive tumors. Said combinations may be administered in certain other embodiments to a patient afflicted by resistant tumors.

Tumor cells as described herein, which the combinations of the invention may be employed to treat, may be apoptosis-resistant, may resist conventional anti-cancer regimens, and/or may be resistant tumors as defined herein. Resistant tumors may, for instance, arise via genetic changes which lead to the reactivation of the Hedgehog pathway despite the presence of Smo inhibitors. Examples are Smo mutations that interfere with inhibitor binding, and/or mutations in genes downstream of Smo that lead to reactivation of the Hedgehog pathway (e.g., sufu, Gli1, Gli2). In these instances of resistant tumors and tumors which do not succumb to conventional anti-cancer regimens, the combinations of the invention can induce tumor cells to undergo senescence, apoptosis, or necrosis. The administration of said combinations can result in tumor cell death and prevention from metastasis.

The methods of the present invention may employ combinations of Smoothened inhibitors as formulated as pharmaceutical preparations comprising a pharmaceutically acceptable excipient or carrier, and cholesterol biosynthesis pathway inhibitors (e.g., statins), Gli inhibitors, and/or Phosphatidylinositol 3-kinase (PI3K) inhibitors. Likewise, said cholesterol biosynthesis pathway inhibitors (e.g., statins), Gli inhibitors, and/or Phosphatidylinositol 3-kinase (PI3K) inhibitors may be formulated as pharmaceutical preparations comprising a pharmaceutically acceptable excipient or carrier as well. Said combinations may be administered to a patient to treat conditions involving unwanted cell proliferation such as cancers and/or tumors (such as medullablastoma, basal cell carcinoma, etc.), and non-malignant hyperproliferative disorders. Said combinations may be administered in certain embodiments to a patient afflicted by sensitive tumors. Said combinations may be administered in certain other embodiments to a patient afflicted by resistant tumors, or to prevent resistant tumors.

Other aspects of the invention provide methods of diagnosing, preventing and/or treating cellular debilitations, derangements, and/or dysfunctions; hyperplastic, hyperproliferative and/or cancerous disease states; and/or metastasis of tumor cells, in a mammal characterized by the presence and/or expression of a Smo gene or gene product (e.g., a Smo protein), comprising administering to a mammal combinations of Smoothened inhibitors and cholesterol biosynthesis pathway inhibitors (e.g., statins), Gli inhibitors, and/or Phosphatidylinositol 3-kinase (PI3K) inhibitors.

Hedgehog Signaling Pathway

Members of the Hedgehog family of signaling molecules mediate many important short- and long-range patterning processes during vertebrate development. Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation. The effects of developmental cell interactions are varied: responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation.

The vertebrate family of Hedgehog genes includes three members that exist in mammals, known as Desert (Dhh), Sonic (Shh) and Indian (Ihh) Hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

Smoothened (Smo) encodes a 1024 amino acid transmembrane protein that acts as a transducer of the Hedgehog (Hh) signal. Smo protein has 7 hydrophobic membrane-spanning domains, an extracellular amino-terminal region, and an intracellular carboxy-terminal region. Smo bears some similarity to G protein-coupled receptors and is most homologous to the Frizzled (Fz) family of serpentine proteins. (Alcedo et al. (1996) Cell 86: 221)

An inactive Hedgehog signaling pathway is where the transmembrane protein receptor Patched (Ptc) inhibits the stabilization, phosphorylation, and activity of Smoothened (Smo). The transcription factor Gli, a downstream component of Hh signaling, is prevented from entering the nucleus through interactions with cytoplasmic proteins, including Fused (Fu) and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc.

Ligand binding by Hh alters the interaction of Smo and Ptc, reversing the repression of Smo, whereupon Smo moves from internal structures within the cell to the plasma membrane. The localization of Smo to the plasma membrane triggers activation of Hh pathway target genes in an Hh-independent manner. (Zhu et al. (2003) Genes Dev. 17(10):1240) The cascade activated by Smo leads to the translocation of the active form of the transcription factor Gli to the nucleus. The activation of Smo, through translocated nuclear Gli, activates Hh pathway target gene expression, including of Wnts, TGFβ, and Ptch and Gli themselves.

Hedgehog Related Disorders

In accordance with the foregoing, the present invention further provides a method for preventing or treating any of the diseases or disorders described herein (also referred to herein as "Hedgehog related disorders," individually or collectively) in a subject in need of such treatment, which method comprises administering to said subject a combination of Smoothened inhibitors (cyclopamine, jervine, compounds of Formula I (e.g., a compound of Formulae (Ia), (Ib) or (Ic)), compounds of Formula II, compounds of Formula III, any of the anti-smoothened compounds individually listed herein, anti-Smo antibodies, and anti-Smo inhibitory nucleic acids (e.g., anti-Smo siRNAs)) or a pharmaceutically acceptable salt thereof, and cholesterol biosynthesis pathway inhibitors (e.g., statins), Gli inhibitors, and/or Phosphatidylinositol 3-kinase (PI3K) inhibitors. For any of the above uses, the required dosage will vary depending on the mode of administration, the particular condition to be treated and the effect desired.

Increased levels of Hedgehog signaling (e.g., aberrant Hedgehog signaling) are sufficient to initiate cancer formation and are required for tumor survival. cancer formation and are required for tumor survival can likewise be due to Ptch loss-of-function, Hedgehog gain-of-function, Smoothened gain-of-function, and/or Gli gain-of-function. These cancers include, but are not limited to, prostate cancer (Karhadkar S S, et al. (2004) Nature. October 7; 431(7009):707-12) (Sanchez P, et al. (2004) PNAS August 24; 101(34):12561-6) (Mimeault M, et al. (2006), International Journal of Cancer; 118 (4):1022-31); breast cancer (Kubo M, et al. (2004) Cancer Res. 2004 Sep. 1; 64(17):6071-4) (Liu S, et al. (2006) Cancer Res; 66 (12):6063-71) (Moraes R C, et al. (2007) Development; 134 (6):1231-42); medulloblastoma (Berman D M, et al. (2002) Science. August 30; 297(5586):1559-61); non-melanoma skin cancer, i.e. squamous cell carcinoma (SCC) and basal cell carcinoma (BCC) (Williams J A, et al. (2003) PNAS April 15; 100(8):4616-21) (Xie J, et al. (1998) Nature. Jan 1; 391(6662):90-2); pancreatic, esophagus, stomach, and biliary cancers (Thayer S P, et al. (2003) Nature. October 23; 425(6960):851-6) (Ma et al. (2006) Int J Cancer 118(1):139) (Berman D M, et al. (2003) Nature. October 23; 425(6960): 846-51) (Nakashima H, et al. (2006) Cancer Research; 66 (14):7041-9) (Feldmann G, et al. (2007) Cancer Research; 67 (5):2187-96) (Ji Z, et al. (2007) J Biol Chem; 282 (19):14048-55), and small-cell lung cancer (Watkins D N, et al. (2003) Nature. March 20; 422(6929):313-7) (Vestergaard J, et al. (2006) Lung Cancer; 52 (3):281-90).

Additional cancers in which increased levels of Hedgehog signaling are sufficient to initiate cancer formation and are required for tumor survival include, but are not limited to colon cancer (Douard R, et al. (2006) Surgery; 139 (5):665-70) (Qualtrough D, et al. (2004) International Journal of Cancer; 110 (6):831-7); glioma (Bar E E, et al. (2007) Neuro-Oncology; 9 (4):594) (Clement V, et al. (2007) Current Biology 17 (2):165-72) (Ehteshan M, et al. (2007) Oncogene; Mar. 12, 2007, Epub ahead of print); melanoma (Stecca B, et al. (2007) PNAS; 104 (14):5895-900); non small cell lung cancer (NSCLC) (Yuan Z, et al. (2007) Oncogene; 26 (7): 1046-55); ovarian (Chen X J, et al. (2007) Cancer Science; 98 (1):68-76); liver (Huang S H, et al. (2006) Carcinogenesis; 27 (7):1334-40) (Sicklick J K, et al. (2006) Carcinogenesis; 27 (4):748-57); renal (Cutcliffe C, et al. (2005) Clinical Cancer Research; 11 (22):7986-94), rhabdomyosarcoma (Hahn H, et al. (1998) Nature Medicine; 4 (5):619-22) (Tostar U, et al. (2006) Journal of Pathology; 208 (1):17-25); and chondrosarcoma (Tiet T D, et al. (2006) American Journal of Pathology; 168 (1):321-30).

Malignant lymphoma (ML) involves the cells of the lymphatic system, and is the fifth most common cancer in the U.S. ML includes Hodgkin's disease, and non-Hodgkin's diseases which are a heterogeneous group of lymphoid proliferative diseases. Hodgkin's disease accounts for approximately 14% of all malignant lymphomas. The non-Hodgkin's lymphomas are a diverse group of malignancies that are predominately of B-cell origin. In the Working Formulation classification scheme, these lymphomas been divided into low-, intermediate-, and high-grade categories by virtue of their natural histories (see "The Non-Hodgkin's Lymphoma Pathologic Classification Project," Cancer 49:2112-2135, 1982). The low-grade lymphomas are indolent, with a median survival of 5 to 10 years (Horning and Rosenberg, N. Engl. J. Med. 311: 1471-1475, 1984). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

Multiple myeloma (MM) is a malignant tumor composed of plasma cells of the type normally found in the bone marrow. These malignant plasma cells accumulate in bone marrow and typically produce monoclonal IgG or IgA molecules. The malignant plasma cells home to and expand in the bone marrow causing anemia and immunosuppression due to loss of normal hematopoiesis. Individuals suffering from multiple myeloma often experience anemia, osteolytic lesions, renal failure, hypercalcemia, and recurrent bacterial infections. MM represents the second most common hematopoietic malignancy.

"Hedgehog related disorders," further comprise cancers of the blood and lymphatic systems, including lymphomas, leukemia, and myelomas. The methods and combinations of the invention antagonize one or more components of the Hedgehog signaling pathway to inhibit growth and proliferation of lymphoma cells, leukemia cells, or myeloma cells. Lymphoma is malignant tumor of lymphoblasts derived from B lymphocytes. Myeloma is a malignant tumor composed of plasma cells of the type normally found in the bone marrow. Leukemia is an acute or chronic disease that involves the blood forming organs. NHLs are characterized by an abnormal increase in the number of leucocytes in the tissues of the body with or without a corresponding increase of those in the circulating blood and are classified according to the type of leucocyte most prominently involved.

By way of example, subjects suffering from or at risk of development of lymphoma (e.g., B-cell lymphoma, plasmoblastoma, plasmacytoma or CLL) can be treated with the methods and combinations of the invention. Preferably, the subject is a human being. The methods and combinations of the invention entail administering to the subject a pharmaceutical composition containing an effective amount of a Smoothened inhibitor in combination with one or more of the following: (i) cholesterol biosynthesis pathway inhibitors (e.g., statins); and (ii) Gli inhibitors. The subject can be one who is diagnosed with lymphoma, with or without metastasis, at any stage of the disease (e.g., stage I to IV, Ann Arbor Staging System). Lymphomas suitable for treatment with methods of the invention include but are not limited to Hodgkin's disease and non-Hodgkin's disease. Hodgkin's disease is a human malignant disorder of lymph tissue (lymphoma) that appears to originate in a particular lymph node and later spreads to the spleen, liver and bone marrow. It occurs mostly in individuals between the ages of 15 and 35. It is characterized by progressive, painless enlargement of the lymph nodes, spleen and general lymph tissue. Classic Hodgkin's disease is divided into four subtypes: (1) nodular sclerosis Hodgkin's disease (NSHD); (2) mixed cellularity Hodgkin's disease (MCHD); (3) lymphocyte depletion Hodgkin's disease (LDHD); and (4) lymphocyte-rich classic Hodgkin's disease (cLRHD).

In some preferred embodiments, the present methods and combinations can be used to treat non-Hodgkin's Lymphoma (NHL). Non-Hodgkin's disease is also called lymphosarcoma and refers to a group of lymphomas which differ in important ways from Hodgkin's disease and are classified according to the microscopic appearance of the cancer cells. Non-Hodgkin's lymphoma includes but is not limited to (1) slow-growing lymphomas and lymphoid leukemia (e.g., chronic lymphocytic leukemia, small lymphocytic leukemia, lymphoplasmacytoid lymphoma, follicle center lymphoma, follicular small cleaved cell, follicular mixed cell, marginal zone B-cell lymphoma, hairy cell leukemia, plasmacytoma, myeloma, large granular lymphocyte leukemia, mycosis fungoides, szary syndrome); (2) moderately aggressive lymphomas and lymphoid leukemia (e.g., prolymphocytic leukemia, mantle cell lymphoma, follicle center lymphoma, follicular small cleaved cell, follicle center lymphoma, chronic lymphocytic leukemia/prolymphocytic leukemia, angiocentric lymphoma, angioimmunoblastic lymphoma); (3) aggressive lymphomas (e.g., large B-cell lymphoma, peripheral T-cell lymphomas, intestinal T-cell lymphoma, anaplastic large cell lymphoma); and (4) highly aggressive lymphomas and lymphoid leukemia (e.g., B-cell precursor B-lymphoblastic leukemia/lymphoma, Burkitt's lymphoma, high-grade B-cell lymphoma, Burkitt's-like T-cell precursor T-lymphoblastic leukemia/lymphoma). The methods of the present invention can be used for adult or childhood forms of lymphoma, as well as lymphomas at any stage, e.g., stage I, II, III, or IV. The methods described herein can also be employed to treat other forms of leukemia, e.g., acute lymphocytic leukemia (ALL).

Some of the therapeutic methods and combinations of the invention are particularly directed to treating lymphomas or myelomas which do not express Gli3. While Gli1 and Gli2 appear to be expressed in all lymphomas, detectable Gli3 expression is present mainly in lymphomas which were resistant to Hh pathway inhibition by cyclopamine. There is no expression of Gli3 in normal spleen B-cells and in the majority of cyclopamine responsive lymphomas.

Thus, prior to treatment with the combinations and methods of the invention, subjects with lymphomas can be first examined for expression of Gli3 in a lymphoma cell sample obtained from the subject. Gli3 expression level in the sample can be compared to Gli3 expression level in normal spleen B cells obtained from the subject. Gli3 expression levels in the lymphoma or myeloma samples and the control cells can be determined using methods well known in the art. A likely responsiveness to treatment with the methods and combinations described herein is indicated by the lack of detectable Gli3 expression in the lymphoma or myeloma samples or an expression level that is not significantly higher (e.g., not more than 25%, 50%, or 100% higher) than Gli3 expression level in the normal B cell. Other than being an additional step of the therapeutic methods of the invention, the pre-screening for lack of Gli3 expression can be used independently as a method for patient stratification.

In addition to lymphomas, the methods and compositions described above are also suitable for the treatment of myelomas. Multiple myeloma is a fatal neoplasm characterized by an accumulation of a clone of plasma cells, frequently accompanied by the secretion of Ig chains. Bone marrow invasion by the tumor is associated with anemia, hypogammaglobinemia, and granulocytopenia with concomitant bacterial infections. An abnormal cytokine environment, principally raised IL-6 and IL-1β levels, often results in increased osteoclasis leading to bone pain, fractures, and hypercalcemia. Despite aggressive chemotherapy and transplantation, multiple myeloma is a universally fatal plasma proliferative disorder.

Combinations and methods of the invention are useful in the treatment of basal cell carcinoma (BCC or rodent ulcer), tumors of the adrenal glands arising from the cortex or the medulla part of the adrenal gland medulla, and ovarian tumors.

Human patients with Gorlin's syndrome (also known as Basal Cell Nevus Syndrome (BCNS) and nevoid basal cell carcinoma), a rare autosomal dominant cancer genetic syndrome, develop basal cell carcinoma (BCC) with high frequency, and other solid tumors (e.g., meduloblastomas) at lower frequency, due to germline loss of function mutations in Ptch. These patients, as well as other, non-Gorlin's patients with BCC who have somatic loss of function mutations in Ptch, and would not be expected to respond to treatments associated with Hedgehog ligands. They would, however, respond to inhibitors of Hh signaling downstream from the Hh ligands, such as found in the methods and combinations of the present invention.

Similarly, other solid tumors due to Ptch or Smo mutations will not respond to Hh ligand-related inhibition but will respond to Smo blockade (e.g., by administration of the methods and combinations of the invention).

A combination of Smoothened inhibitors (e.g., a compound of Formula I, Formula II, or Formula III, or any of the compounds listed herein or incorporated by reference) or a pharmaceutically acceptable salt thereof, and cholesterol biosynthesis pathway inhibitors (e.g., statins), Gli inhibitors, and/or Phosphatidylinositol 3-kinase (PI3K) inhibitors of the invention are also useful in the treatment of Hedgehog related disorders that include bone overgrowth disorders. Bone overgrowth disorders include, but are not limited to, acromegaly, macrocephaly, Sotos syndrome, progressive diaphyseal dysplasia (PDD or Camurati-Engelmann disease), craniodiaphyseal dysplasia, and endosteal hyperostosis disorders including Van Buchem disease (types I and II) and sclerosteosis.

Combinations of the invention are useful in the treatment of unwanted hair growth, for example, hairy moles and cosmetic prevention of hair regrowth after epilation.

Combinations of the invention are also useful in the treatment of such Hedgehog related disorders as psoriasis, which other known Hedgehog pathway inhibitors (e.g. cyclopamine) have shown utility in treating (Cutis, 2006, 78(3):185-8; Br. J. Dermatology April; 154(4):619-23.

Combinations of the invention are also useful in the treatment of such Hedgehog related disorders as "fibrotic disorders," particularly liver fibrosis. Fibrotic disorders are characterized by excessive fibroblast or myofibroblast proliferation and production of connective tissue matrix, including collagen, fibronectin and glycosaminoglycans (GAG). Liver fibrotic disorders include but are not limited to alcoholic, Hepatitis C-associated, and primary biliary fibrosis, as well as non-alcoholic steatosis, sclerosing cholangitis, and fibrosis resulting from schistosomiasis.

Hedgehog signaling is important for T-cell differentiation, as evidenced at least by Shh−/− mice having small thymus size, and showing reduced double negative to double positive T-cell differentiation. In addition to the proliferation and differentiation of T-cell progenitor cells, Hh signaling is shown to modulate T-cell receptor signaling during repertoire selection. Consequently, the methods and combinations of the invention can be useful for the treatment and diagnosis of T-cell associated disorders such autoimmune and inflammatory diseases, and in immune system evasion by tumours.

Gli Transcription Factors

Zinc-finger transcription factors Gli1, Gli2, and Gli3 are the ultimate effectors of the Hedgehog signaling pathway, to which Smoothened transduces its signal upon release from Patched inhibition (e.g., upon Hedgehog ligand binding). Gli is implicated in tumorigenesis, and its constitutive activation is critically important for cancer development. (Lauth, M. et al. (2007) PNAS 104(20): 8455).

Data described herein suggests that amplification of the down-stream transcription factor Gli2 may be responsible for reactivation of the Hedgehog pathway despite the presence of smo inhibitors (which can lead to, e.g., the formation of resistant tumors) Inhibitors that act on Gli1 or Gli2 are thought to inhibit growth of resistant tumors, particularly in combination with Smoothened inhibitors, as provided by the present methods of the invention.

Known Gli inhibitors that can be used in the combination methods of the invention include, but are not limited to, small molecule Gli antagonists GANT61 (Gli-ANTagonist 61) and GANT58 (Laugh, M. et al.). Other known Gli inhibitors that can be used in the combination methods of the invention include, but are not limited to, sesquiterpenes zerumbone and zerumbone epoxide; bisindole alkaloids staurosporinone, 6-hydroxystaurosporinone, arcyriaflavin C, and 5,6-dihydroxyarcyriaflavin A; and physalins F and B. (Hosoya, T. et al. (2008) ChemBioChem 9:1082).

PI3Ks

The phosphatidylinositol 3-kinases (PI3Ks) are widely expressed lipid kinases that phosphorylate phosphoinositides at the D-3 position of the inositol ring. These proteins function as signal transducers downstream of cell-surface receptors. The products of PI3K-catalyzed reactions, phosphatidylinositol 3,4,5-trisphosphate (PtdIns(3,4,5)P3), phosphatidylinositol 3,4-bisphosphate (PtdIns(3,4)P2), and phosphatidylinositol 3-phosphate (PtdIns(3)P), are second messengers which have central roles in a number of cellular processes, including cell growth, differentiation, mobility, proliferation and survival.

The eight members of the PI3K family have been classified into three groups based on their primary sequence, in vitro substrate preference, domain structure, and mode of regulation. Class II PI3Ks are predominantly associated with membrane fractions of cells, are characterized by a C2 domain at their C-terminus, and consist of three iso forms (PI3K-C2a, PI3K-C2β, and PI3K-C2γ). (Sheikh, et al. (2003) BMC Clin. Pathol. 3:1). Class III PI3Ks utilize only phosphatidylinositol as a substrate, and play an essential role in protein trafficking through the lysosome. (Volinia, et al. (1995) EMBO J. 14:3339).

Class I PI3Ks, which are the subject of the methods and combinations of the present application, are composed of two subgroups, IA and IB. The class IA PI3K subgroup consists of there catalytic subunits, p 110α, p110β and p110δ, that form heterodimers with one of five regulatory domains: p85α, p85β, p85γ, p50α and p55α. These PI3Ks are activated by cell surface receptor tyrosine kinases.

The Class IB PI3K consists of one member, a heterodimer of p110g, and a regulatory p101 domain, that is activated by G-proteins βγ subunits following the stimulation of G-protein coupled receptors. PI3Ks IA and IB catalyze the formation of PtdIns(3,4,5)P3, a process that is reversed by the action of the lipid phosphatase, PTEN.

Cholesterol Synthesis Pathway

Among the reasons the Hedgehog and cholesterol biosynthesis pathways are linked is that sterol synthesis is required for Shh signal transduction. (Corocoran, R. and Scott, M. (2006) PNAS 103(22):8409). Not only is the Shh ligand covalently modified by cholesterol, but Shh signaling can be blocked at receiving cells in the Hedgehog pathway when sterol synthesis is impaired. (Cooper, M. et al. (1998) Science 280:1603). The antitumoral effects of statins are well known in the art, and several statins are in clinical trials for cancer indications. A connection between cholesterol and cancer has been suggested by studies using the statin class of cholesterol synthesis inhibitors. (Bar, E. & Stearns, D. (2008) Expert Opin. Investig. Drugs 17(2):185). Statins bind HMG-CoA (the enzyme 3-hydroxy-3-glutaryl-coenzyme A) reductase roughly 1000 times more effectively than the natural substrate.

Combinations of Smoothened Inhibitors with Cholesterol Biosynthesis Pathway Inhibitors, Phosphatidylinositol 3-Kinase (PI3K) Inhibitors, and/or Gli Inhibitors The invention provides for a combinations of Smoothened inhibitors (e.g., a compound of Formula I, Formula II, or Formula III, or any of the compounds listed herein or incorporated by reference) and cholesterol biosynthesis pathway inhibitors (e.g., statins), Gli inhibitors, and/or Phosphatidylinositol 3-kinase (PI3K) inhibitors. This combination can be provided as a pharmaceutical combinations, e.g. a kit, comprising a) a first agent which is a Smoothened inhibitors (e.g., a compound of Formula I, Formula II, or Formula III, or any of the compounds listed herein or incorporated by reference) as disclosed herein, in free form or in pharmaceutically acceptable salt form, and b) at least one co-agent which comprises a cholesterol biosynthesis pathway inhibitors (e.g., statins) and/or a Gli inhibitors. The kit can comprise instructions for its administration.

Synergistic effects are possible with the combinations of the invention—i.e., the therapeutic effects of the combination of Smoothened inhibitors (e.g., a compound of Formula I, Formula II, or Formula III, or any of the compounds listed herein or incorporated by reference) and cholesterol biosynthesis pathway inhibitors (e.g., statins), Gli inhibitors, and/or Phosphatidylinositol 3-kinase (PI3K) inhibitors can be significantly greater than the therapeutic effects of each inhibitor administered individually, or even than the expected mere additive effects of combining them. In some embodiments, the combined agents are administered simultaneously. In other embodiments, the combined agents are administered sequentially.

The dosages of the co-administered agents will vary depending on the specific type of agent employed, on the condition being treated and so forth.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a Smoothened inhibitor compound and a co-agent, are both administered to a patient simultaneously in the form of a single entity or dosage. The term "non-fixed combination" means that the active ingredients, e.g. a Smoothened inhibitor compound and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Administration and Pharmaceutical Compositions:

The invention relates to the use of combinations of pharmaceutical compositions comprising Smoothened inhibitors (e.g., a compound of Formula I, Formula II, or Formula III, or any of the compounds listed herein or incorporated by reference), and cholesterol biosynthesis pathway inhibitors (e.g., statins), Gli inhibitors, and/or PI3K inhibitors for the therapeutic (and, in a broader aspect of the invention, prophylactic) treatment of Hedgehog-related disorder(s) such as cancers.

In general, compounds of the methods and combinations of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 1000 mg, preferably 500 mg, more preferably 100 mg, conveniently administered, e.g. in divided doses up to four times a day or in retard form. Suitable unit dosage forms for oral administration comprise from ca. 1 to 50 mg active ingredient.

Compounds of the methods and combinations of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions.

Compounds may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

EXAMPLES

The present invention is further exemplified, but not limited, by the following representative examples, which are intended to illustrate the invention and are not to be construed as being limitations thereon. Unless otherwise indicated, said examples employ the following materials and methods:
Description of Subcutaneous Medulloblastoma Allograft Models Mouse medulloblastoma cells ($1.0$–$5.0 \times 10^6$), dissociated directly from tumor fragments originally derived from spontaneously arising medulloblastomas in Ptch+/−p53−/−, Ptch+/−Hic+/− or Ptch+/− mice, were inoculated subcutaneously into the right flank of Harlan nu/nu mice. Treatment was initiated approximately 7-10 days post implantation. Animals were randomized into treatment groups with similar mean tumor volumes that ranged from approximately 250-300 mm3. Tumor volumes (mm3) and body weights (g) were recorded two or three times per week from all groups for analysis. Dose was body weight adjusted at time of dosing. Comparisons between treatment groups was performed using a non-parametric Kruskal-Wallis/Wilcoxon Rank Sum Test.
Allograft Model Data Analysis Tumors were calipered in two dimensions, and the volumes were calculated using the formula: (length×width2)/2, where length is the longer of the two measurements and width is the shorter one. Percent treatment/control (% T/C) values were calculated using the following formula: % T/C=100×ΔTf-i/ΔCf-i if ΔTf-i>0, % T/T0=100×ΔTf-i/T0 if ΔTf-i<0 (regression). A partial responder (PR) was defined as an animal whose tumor was less than 50% of the initial tumor volume by the end of the study. An animal with no palpable tumor by the end of study is defined as a complete responder (CR).

Example 1

Drug Resistance Observed in Ptch+/− Models

Ptch+/− mice develop medulloblastoma spontaneously (Romer, et al 2004). The tumors, which have been previously shown to be Smo-dependent, are used as models to test compounds which inhibit the Hh pathway. The loss of p53 results in an earlier onset and increases the incidence rate of medulloblastomas, where 95% of Ptch+/−p53−/− mice develop medulloblastoma and most die from brain tumors within 12 weeks of birth (Wetmore, Eberhart and Curran 2001, Romer, et al 2004). Ptch+/−Hic+/− mice also form medulloblastomas with increased penetrance and decreased latency (Briggs et al., 2008) Smo inhibitors have been shown to effectively decrease the incidence of medulloblastoma in Ptch+/−p53−/− mice, both directly in the transgenic model (Romer, et al 2004) and in allograft models derived from the Ptch+/−p53−/− medulloblastoma tumors (Berman, et al. 2002).

Therefore the in vivo efficacy of Compound 1 was evaluated in Ptch+/−p53−/−, Ptch+/−Hic+/− and Ptch+/− mouse medulloblastoma allograft models, derived from corresponding transgenic mice and passaged in vivo, and following long-term continuous dosing.

Example 1a

Treatment in the Ptch+/−p53+/− Medulloblastoma Allograft Model

Treatment in the Ptch+/−p53+/− model occurred as follows: Treatments started on day 8 post implantation (5 million cells/animal). Compound 1 was administered po (i.e., orally) at 5 mg/kg bid (i.e., twice a day), 10 mg/kg bid, 20 mg/kg qd (i.e., once a day), 20 mg/kg bid, 40 mg/kg bid and 80 mg/kg bid for 25 days total. Compound 2 was administered at 100 mg/kg bid for 25 days. Vehicle control of Compound 1 was 0.5% methylcellulose 0.5% Tween 80 in water. The initial group size consisted of 8 animals. The vehicle group was taken down 10 days after treatment (tumors greater than 10% of mouse body weight). Animals were dosed continuously for a total of 26 days treatment.

Following said continuous dosing for 26 days (FIG. 1), tumor regression was observed during the first half of the dosing period. Afterwards, however, tumors regrew even though dosing was continued. Likewise, Compound 2 dosed at 100 mg/kg bid also initially caused regression, followed by tumor regrowth. Expression of Gli1 mRNA was analyzed in the regrown tumors at the end of dosing and shown to be only partially suppressed (60 to 80% compared to vehicle control). Internal previous studies have shown that close to 100% Gli1 mRNA inhibition is required for tumor regression. This suggests that the tumor regrowth is due to insufficient inhibition of the Hedgehog pathway as analyzed by the pharmacodynamic marker Gli1 mRNA.

Example 1b

Treatment in the Ptch+/−Hic+/− Medulloblastoma Allograft Model

Figure 2:
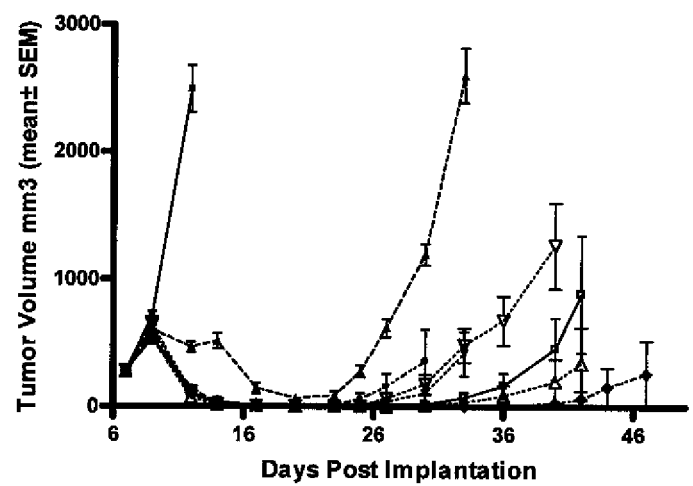
FIG. 2 shows the anti-tumor activity of Compounds 1 and 2 and resistance to Compounds 1 and 2 in the Ptch+/−Hic+/− medulloblastoma allograft model following continuous treatments.

In a follow up study in the Ptch+/−Hic+/− model, the results of which are shown in FIG. 2, treatment occurred as follows:

Treatments started on day 7 post implantation (5 million cells/animal). Compound 1 was administered po at 5 mg/kg bid, 10 mg/kg bid, 20 mg/kg qd, 20 mg/kg bid, 40 mg/kg bid and 80 mg/kg bid for the length of study. Compound 2 was administered at 100 mg/kg bid for the length of study. Vehicle control of Compound 1 was 0.5% methylcellulose 0.5% Tween 80 in water. The initial group size consisted of 8 animals. The vehicle group was taken down 10 days after treatment (tumors greater than 10% of mouse body weight).

In the Ptch+/−Hic+/− model, some but not all of the tumors showed evidence of regrowth following the initial regression. However sustained complete regressions were observed in a subset of animals (see Table 1). Sustained complete responses appeared to be more frequent at higher doses. This suggests that resistance develops to varying degrees in different subcutaneous allograft mouse tumor models which share the Ptch+/− mutation but have different tumor suppressor mutations (p53−/− or Hic+/−).

As seen in both FIG. 2 and Table 1, Ptch+/−Hic+/− tumors were all dosed with Compound 1 at 5,10, 20, 40 and 80 mg/kg bid and 20 mg/kg qd, and Compound 2 at 100 mg/kg bid po starting 7 days post implantation. Sustained regressions listed in the Table 1 represent number of complete responses still present at the end of study on day 47.

Within FIG. 2, filled squares represent vehicle only, po bid (i.e., orally, twice a day). Filled triangles with dotted lines represent Compound 2, administered 100 mg/kg po bid. Upside-down filled triangles with dotted lines represent Compound 1, administered 5 mg/kg po bid. Filled diamonds with dotted lines represent Compound 1, administered 10 mg/kg po bid. Filled circles with dotted lines represent Compound 1, administered 20 mg/kg po qd. Open squares with dotted lines represent Compound 1, administered 20 mg/kg po bid. Open triangles with dotted lines represent Compound 1, administered 40 mg/kg po bid. Open upside-down triangles with dotted lines represent Compound 1, administered 80 mg/kg po bid.

TABLE 1 regression in Ptch+/−Hic+/− medulloblastoma model

| Groups | Ptch+/−Hic+/− |
| --- | --- |
| Vehicle | 0/8 |
| Compound 1 5 mg/kg bid | 0/8 |
| Compound 1 10 mg/kg bid | 1/8 |
| Compound 1 20 mg/kg bid | 7/8 |
| Compound 1 20 mg/kg qd | 0/8 |
| Compound 1 40 mg/kg bid | 3/8 |
| Compound 1 80 mg/kg bid | 6/8 |
| Compound 2 100 mg/kg bid | 0/8 |

Two additional Smo inhibitors, Compound 3 and Compound 4 were evaluated in follow-up studies in the Ptch+/−Hic+/− model upon continous dosing. Both initially induced tumor regression followed by tumor regrowth in the presence of compound. The following number of sustained complete regressions were observed for Compound 3: 0/8 at 40 mg/kg qd, 3/8 at 40 mg/kg bid, 0/8 at 60 mg/kg qd, 0/8 at 80 mg/kg qd, 3/8 at 100 mg/kg qd (mice were dosed from day 10 post tumor implant to day 56, sustained regressions are listed for day 56). No sustained regressions were observed for Compound 4 (mice were dosed from day 8 post tumor implant to day 43.

Example 1c

Treatment in the Ptch+/− Medulloblastoma Allograft Model

Figure 3:
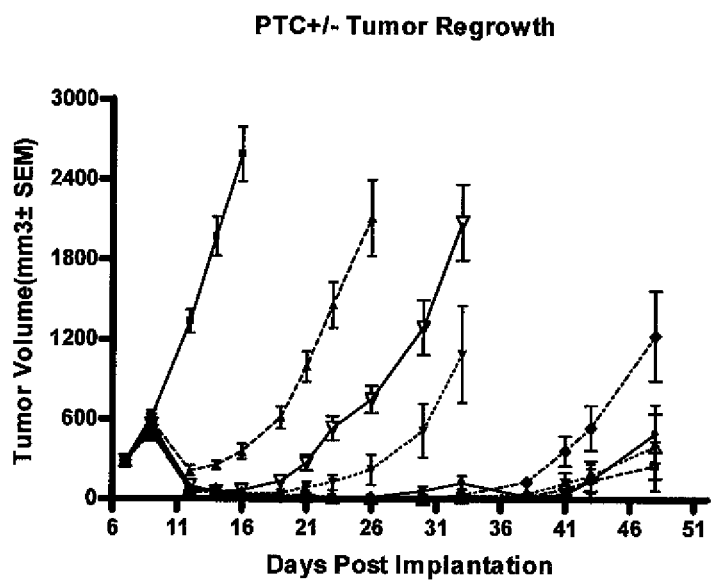
FIG. 3 shows the anti-tumor activity of Compounds 1 and 2 and resistance to Compounds 1 and 2 in the Ptch+/− medulloblastoma allograft model following continuous treatment As described in greater detail below.

In these studies, treatment occurred as follows, the results of which are shown in FIG. 3:

Treatments started on day 7 post implantation (5 million cells/animal). Compound 1 was administered po at 10 mg/kg qd, 20 mg/kg qd, 40 mg/kg qd, 80 mg/kg qd and 160 mg/kg qd for the length of study. Compound 2 was administered at 100 mg/kg bid for the length of study. Vehicle control of Compound 1 was 0.5% methylcellulose 0.5% Tween 80 in water. The initial group size consisted of 8 animals. The vehicle group was taken down 7 days after treatment (tumors greater than 10% of mouse body weight). Similar resistance was seen to that observed with the Ptc+/−Hic+/− model, with a subset of the complete responders growing back and others showing complete regression (Table 2). Sustained regression listed in Table 2 represent number of complete regressions still present at the end of study on day 48.

TABLE 2

Sustained regressions in Ptch+/− model

| Groups | Ptch+/− |
| --- | --- |
| Vehicle | 0/8 |
| Compound 1 10 mg/kg qd | 0/8 |
| Compound 1 20 mg/kg qd | 1/8 |
| Compound 1 40 mg/kg qd | 1/8 |
| Compound 1 80 mg/kg qd | 4/8 |
| Compound 1 160 mg/kg qd | 5/8 |
| Compound 2 100 mg/kg bid | 0/8 |

Within FIG. 3, filled squares represent vehicle only, qd bid (i.e., orally, once a day). Filled triangles with dotted lines represent Compound 1, administered 10 mg/kg po qd. Upside-down filled triangles with dotted lines represent Compound 1, administered 20 mg/kg po qd. Filled diamonds with dotted lines represent Compound 1, administered 40 mg/kg po qd. Filled circles with solid lines represent Compound 1, administered 40 mg/kg po bid. Open squares with dotted lines represent Compound 1, administered 80 mg/kg po qd. Open triangles with dotted lines represent Compound 1, administered 160 mg/kg po qd. Open upside-down triangles with dotted lines represent Compound 2, administered 200 mg/kg po bid.

Example 2

Characterization of Mechanism of Drug Resistance

In order to characterize changes in gene expression in sensitive tumors compared to resistant tumors (both of which terms are defined herein), RNA was isolated from sensitive tumors treated with vehicle or Compound 1 for 4 (single dose), 16 (single dose) and 48 hours (three doses) as well as from resistant tumors (that initially had regressed in the presence of Compound 1 (day 13) but then regrew in the presence of drug as described above). Three tumors were analyzed per treatment group: The sensitive tumor group comprises tumors treated with 20 mg/kg of Compound 1 for 4 hours; 16 hours; and 48 hours. The resistant tumor group comprises tumors treated with 10 mg/kg bid and 80 mg/kg bid of Compound 1 for 26 days.

mRNA expression in tumor samples was analyzed by Affymetrix profiling. The expression data were analyzed using the GeneGo pathway program, which groups data according to signal transduction pathways. It was observed that genes which are indicative of the Hedgehog signaling pathway activity were suppressed in sensitive tumors in a time-dependent manner upon treatment with Compound 1 for 4 h, 16, and 48 h. In resistant tumors (that initially had regressed in the presence of Compound 1 (day 13) but than regrew in the presence of drug) the expression of Hedgehog pathway genes was close to the expression in vehicle treated tumors indicating that Compound 1 no longer sufficiently inhibited the expression of Hedgehog pathway genes. A similar expression pattern was observed for genes of the Cholesterol biosynthesis pathway. A different expression pattern was observed for genes indicative of PI3K pathway activity. No changes in gene expression were detected in sensitive tumors upon treatment with Compound 1 for 4, 16 and 48 h. However, upregulation of PI3K pathway activity was observed in resistant tumors, as compared to sensitive tumors.

Example 2a

Characterization of Mechanism of Hedgehog Pathway Reactivation

One proposed mechanism of action is that genetic changes in resistant tumors lead to the reactivation of the Hedgehog pathway despite the presence of Smo inhibitors. Examples are Smo mutations that interfere with inhibitor binding, and/or mutations in genes downstream of Smo that lead to reactivation of the Hedgehog pathway (e.g., Sufu, Gli1, Gli2).

DNA was isolated from resistant tumors and from sensitive tumors, on which sequencing analysis was performed. No mutations were detected in Sufu, Smo, Gli1 and Gli2 specific for resistant versus sensitive tumors.

Figure 4:
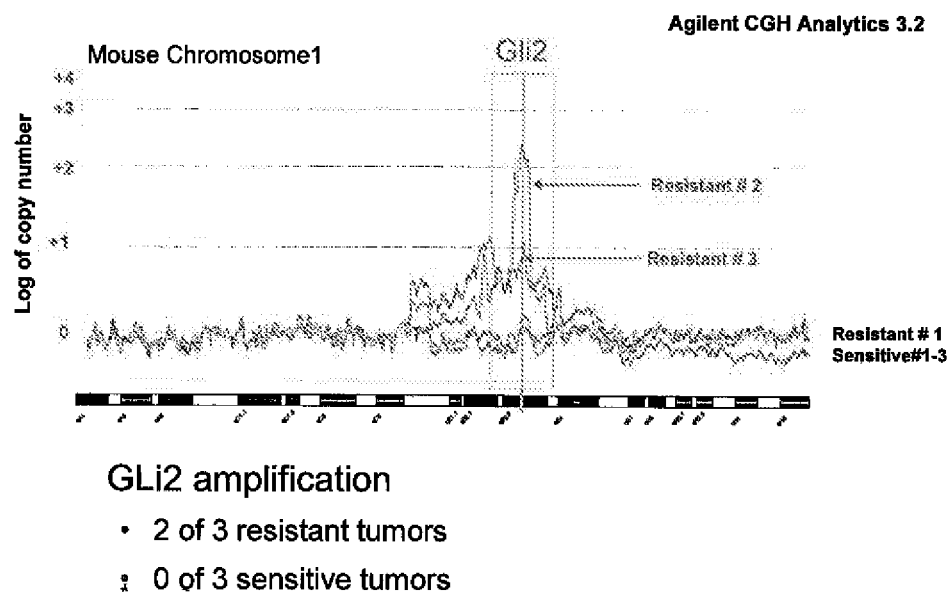
FIG. 4 shows the amplification of Gli2, as detected in 2 of 3 resistant tumors.

DNA from 3 sensitive and 3 resistant Ptch+/−p53−/− tumors was also isolated and analyzed for genome-wide amplification or deletions using the Agilent CGH Analytics 3.2 oligo array. Liver DNA from Ptch+/−p53−/− mice was used as comparison. As seen in FIG. 4, amplification of Gli2 was detected in 2 of 3 resistant tumors and in none of the sensitive tumors.

In order to analyze copy number of Gli2 in all resistant tumors a quantitative PCR for Gli2 was developed (as well as for Gli1 and Gli3). Amplification of Gli2 was detected in a large percentage of resistant tumors in the Ptch+/−p53−/− model (24 out of 44 resistant tumors) but to a lesser extent in the Ptch+/− model (10%). Gli2 amplification was not detected in the Ptch+/−Hic+/− model.

The data suggest that amplification of the down-stream transcription factor Gli2 might be responsible for re-activation of the Hedgehog pathway in the presence of smo inhibitors in some of the resistant tumors. Inhibitors that act on Gli1 or Gli2 might be able to inhibit growth of resistant tumors.

Example 2b

Characterization of Mechanism of Cholesterol Biosynthesis Pathway Inhibition Upregulation of the cholesterol biosynthesis pathway may contribute to the reactivation of the Hedgehog pathway in resistant tumors. Oxysterols have been implicated previously as signaling mediators in the Hedgehog pathway. (Corcoran, et al. (2006) PNAS 103(22): 8408) Increased oxysterol levels in the cell may interfere with the inhibition of Smo activity by Smo inhibitors, either by directly competing for binding sites on Smo or by indirectly interfering with inhibitor binding. Inhibition of the cholesterol biosynthesis pathway by statins could inhibit the growth of resistant tumors, or could prevent the development of resistance either alone or in combination with smoothened inhibitors.

The effect of statins (e.g., simvastatin, flustatin) on the proliferation of medulloblastoma cells derived from sensitive and resistant Ptch+/− cells was evaluated by using an "ex-vivo medulloblastoma proliferation assay." Using Ptch+/−p53−/−, Ptch+/−Hic+/− or Ptch+/− medulloblastoma tumors freshly harvested from allografted nude mice, we have developed a short-term 48 h proliferation assay that enables us to assess the in vitro potency of Smo inhibitors. The read-out for proliferation uses incorporation of 3H thymidine. The assay reflects the in vivo sensitivity of tumor cells to Compound 1. Sensitive tumor cells were inhibited by compound 1 with an IC50 of 4 nM whereas the IC50 in resistant tumors was greater than 20 uM.

As seen in Table 3, both sensitive as well as resistant tumor cells are inhibited by the cholesterol biosynthesis pathway inhibitors Simvastatin with an IC50 in the low nanomolar range. This suggests that statins might be able to inhibit the growth of resistant medulloblastoma tumors in vivo or that the combination of Smo inhibitors with statins might be able to prevent the development of resistance.

TABLE 3

| Tumor type | Compound 1 IC50 (uM) | Compound A IC50 (uM) | Simvastatin IC50 (uM) |
|---|---|---|---|
| Sensitive tumor | 0.003 | 0.2 | 0.004 |
| Resistant tumor | >20 | 0.22 | 0.004 |

Example 2c

Administration of PI3K Pathway Inhibitors

Compound A, an inhibitor of PI3 kinase, was used to evaluate the role of the PI3 kinase pathway in medulloblastoma. Table 4 summarizes the results of treating medulloblastomas with Compound 1 (a Smoothened inhibitor compound of Formula II), Compound A (a PI3K inhibitor compound of Formula A), or combinations thereof. Compound A is capable of inhibiting the lipid kinase activity of PI3K. Among other effects, Compound A is known to inhibit the phosphorylation and activation of the downstream effector Aid and S6 in both sensitive and resistant cells (shown in FIG. 5).

TABLE 4

| Exp | Genotype | Tumor type | Compound 1 (uM) | Compound A (uM) | Compound 1 + A (uM) |
|---|---|---|---|---|---|
| 120707 | ptch+/−Hic+/− | sensitive | 0.004 | 0.3 | nd |
| 120707 | ptch+/−Hic+/− | Resistant | >20 | 0.15 | nd |
| 021908 | ptch+/−Hic+/− | sensitive | 0.002 | 0.11 | nd |
| 020508 | ptch+/−Hic+/− | Resistant | >20 | 0.3 | nd |
| 031708 | ptch+/−Hic+/− | Resistant | >20 | 0.17 | 0.17 (5 uM 225) 0.001 (20 uM 225) |

* PI3K class I inhibitor (alpha, beta, and delta)

The effect of PI3K inhibitors (e.g., compounds such as Compound A) on the proliferation of medulloblastoma cells derived from sensitive and resistant medulloblastoma cells was evaluated by using an "ex-vivo medulloblastoma proliferation assay," as described above. As shown in Table 4, sensitive cells were inhibited by compound 1 with an IC50 of 2 to 4 nM whereas the IC50 was greater than 20 μM in resistant tumors. However, the PI3 kinase inhibitor Compound A inhibited both sensitive and resistant tumors with similar IC50s.

Figure 5:
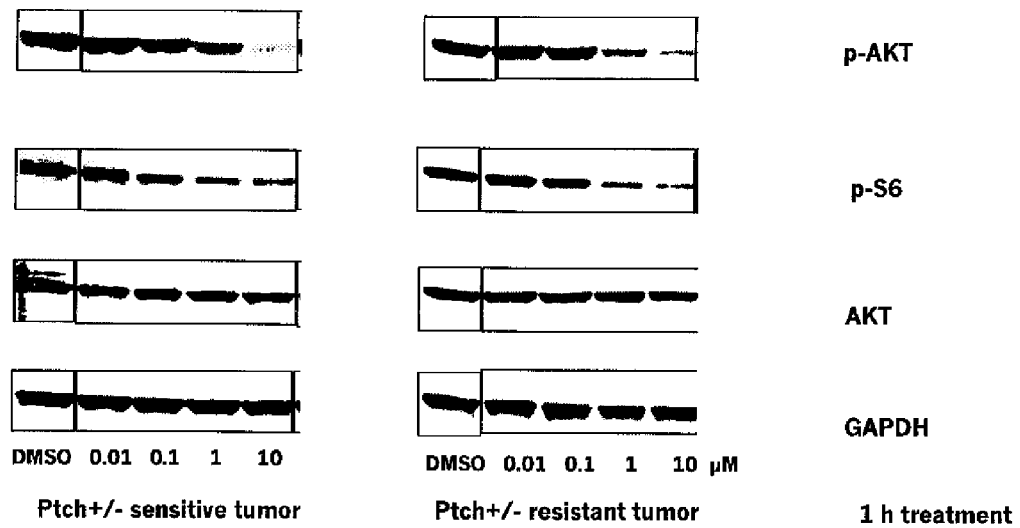
FIG. 5 is a Western blot which demonstrates the results of an ex-vivo medulloblastoma assay, the details of which are described below. As seen in the Western blot, a PI3K inhibitory compound, Compound A, inhibits Akt and S6 phosphorylation in both sensitive and resistant cells.

As shown in FIG. 5, Compound A inhibited Akt and S6 phosphorylation both in sensitive and resistant tumors at similar concentrations. This shows the correlation of inhibition of the PI3 kinase pathway and inhibition of proliferation.

Figure 6A:
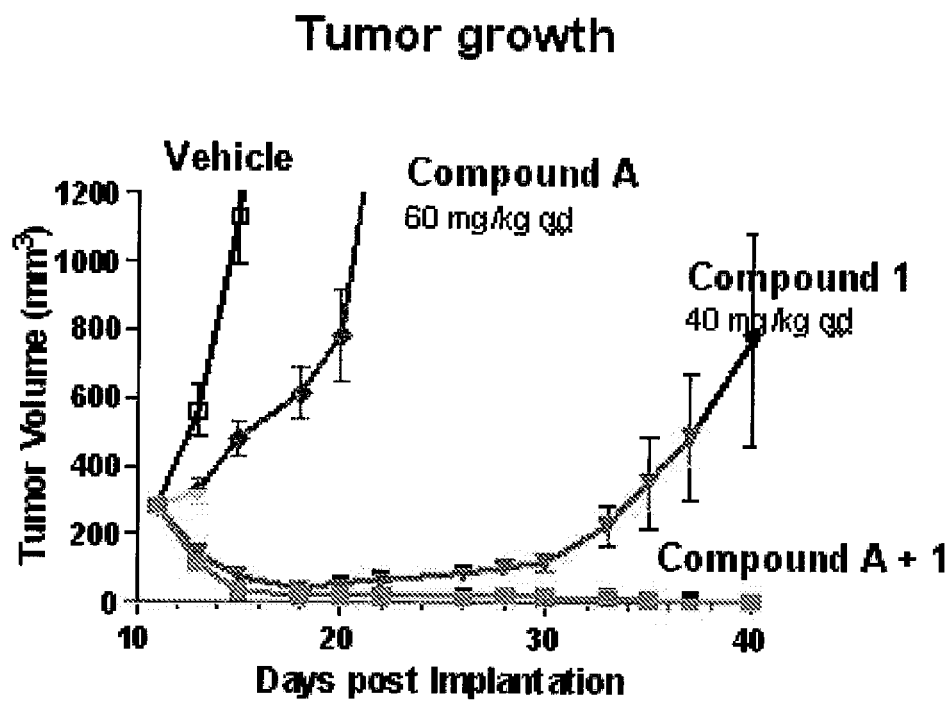
FIGS. 6A and 6B show the effects of a combination of Compound A and Compound 1 on Ptc+/−Hic+/− allograft model, and demonstrates that the combination prevents or delays resistance in said medulloblastoma model.

Next, a combination of Compound 1 and Compound A was explored in the Ptch+/−Hic+/− medulloblastoma allograft model. As shown in FIG. 6A, animals were dosed with 40 mg/kg qd of Compound 1, 60 mg/kg qd of Compound A, and a combination of Compound 1 and Compound A. Whereas Compound A had only a moderate effect on tumor growth compared to vehicle control, Compound 1 initially induced regression but tumors started to regrow. No tumor regrowth was observed in animals treated with the combination of Compound 1 and Compound A.

Figure 6B:
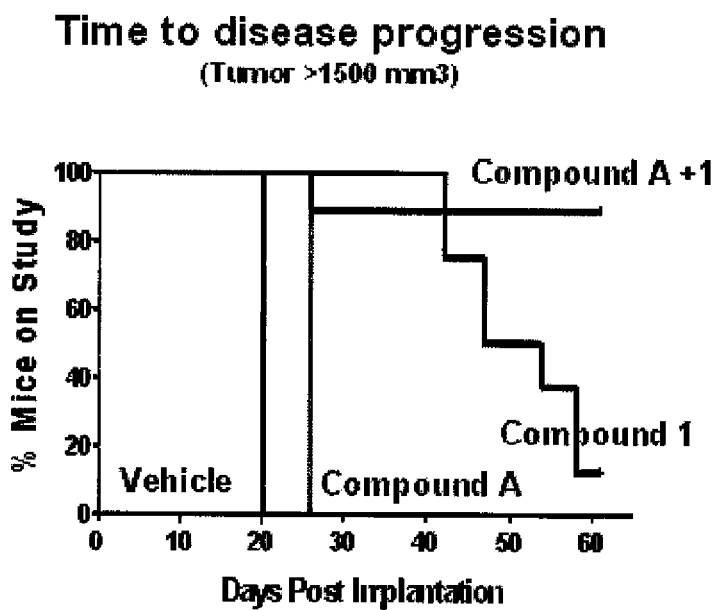

The combination treatment resulted in prolonged time to endpoint (tumor volume >1500 mm3), as shown in FIG. 6B. Animals treated with vehicle control and with compound A had to be sacrificed around day 20 and 25, respectively, because their tumor volume reached 1500 mm3. The time to endpoint was significantly prolonged in animals treated with Compound 1. In the combination treatment group the majority of mice remained on study. Similar results were obtained for animals treated with Compound 1 alone for the first 10 days, followed by single agent treatment with Compound A (data not shown). The data indicate that the combination of Smo inhibitors and PI3K inhibitors can significantly delay or prevent the development of resistance in the medulloblastoma model.

Figure 7A:
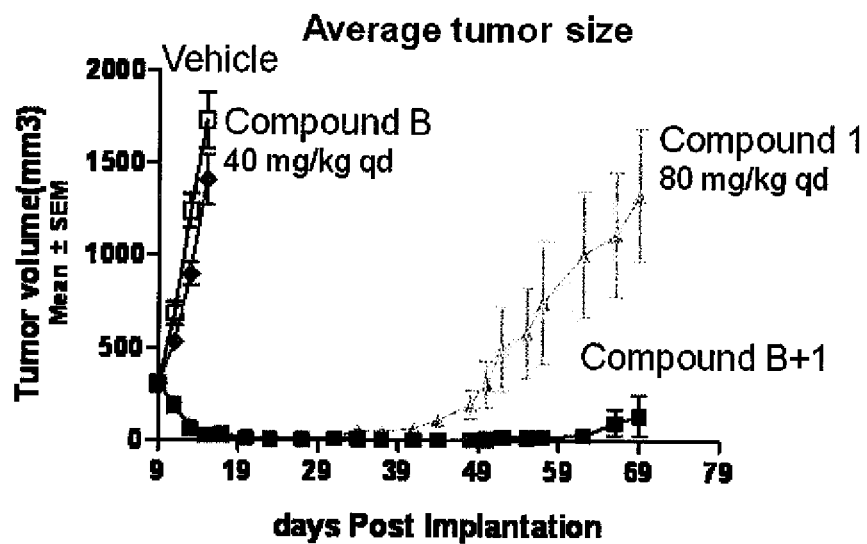
FIGS. 7A and 7B show the effects of a combination of Compound B and Compound 1 on Ptc+/−Hic+/− allograft model, and demonstrates that the combination prevents or delays resistance in said medulloblastoma model.

Next, a combination of Compound 1 and Compound B was explored in the Ptch+/−Hic+/− medulloblastoma allograft model. As shown in FIG. 7A, animals were dosed with 80 mg/kg qd of Compound 1, 40 mg/kg qd of Compound B, and a combination of Compound 1 and Compound B. Whereas Compound B had no effect on tumor growth compared to vehicle control, Compound 1 initially induced regression but tumors started to regrow. Tumor regrowth in animals treated with the combination of Compound 1 and Compound B was considerably delayed.

Figure 7B:
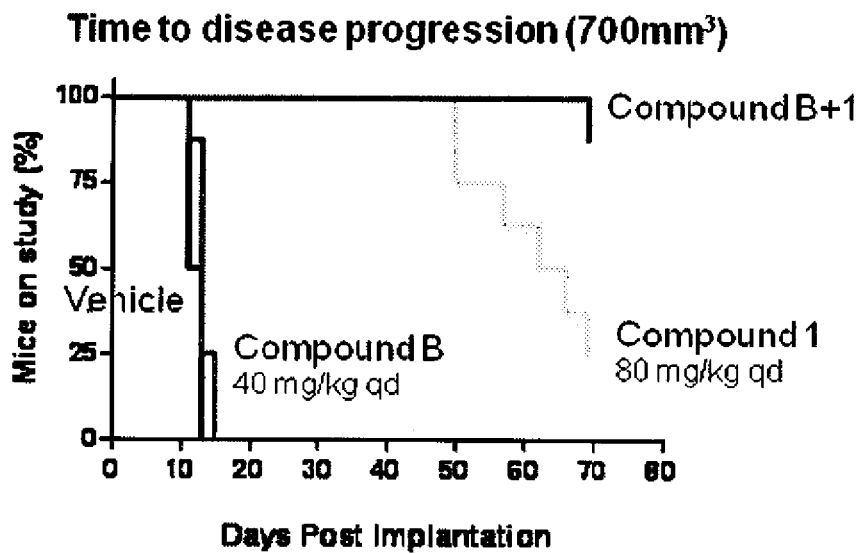

The combination treatment resulted in prolonged time to endpoint (tumor volume >700 mm3), as shown in FIG. 7B. Animals treated with vehicle control and with compound B reached the endpoint around day 12 to 15, respectively, because their tumor volume reached 700 mm3. The time to endpoint was significantly prolonged in animals treated with Compound 1. In the combination treatment group the majority of mice remained on study. The data indicate that the combination of Smo inhibitors and PI3K inhibitors can significantly delay or prevent the development of resistance in the medulloblastoma model.

What is claimed is:

1. A method for treating a brain cancer or tumor selected from medulloblastoma, glioblastoma or glioma in a patient in need thereof comprising administering to the patient a Smoothened inhibitor and a PI3 kinase inhibitor, wherein the Smoothened inhibitor is 2-methyl-4'-trifluoromethoxy -bipheny-3-carboxylic acid [6-(cis-2,6-dimethyl-morpholin-4-yl)-pyridin-3-yl]-amide or a pharmaceutically acceptable salt thereof and the PI3 kinase inhibitor is 5-(2,6-di-morpholin-4-yl-pyrimidin-4-yl)-4-trifluoromethyl-pyridin-2-vlamine, 2-methyl-2-[4-3-methyl-2-oxo-8-quinolin-3-yl-2,3-dihydro-imidazo[4,5-c]quinolin-1-yl) -phenyl]-propionitrile, or 8-(6-methoxy-pyridin-3-yl)-3-methyl-1-(4-piperazin-1-yl-3-trifluoromethyl -phenyl)-1,3-dihydro-imidazol[4,5-c]quinolin-2-one, or a pharmaceutically acceptable salt thereof.

2. The method of claim 1, wherein the medulloblastoma is from a resistant tumor.

3. The method of claim 1, wherein the PI3 kinase inhibitor is 5-(2,6-di-morpholin-4-yl -pyrimidin-4-yl)-4-trifluoromethyl-pyridin-2-ylamine.

4. The method of claim 1, wherein the PI3 kinase inhibitor is 2-methyl-2[4-(3-methyl -2-oxo-8-quinolin-3-yl-2,3-dihydro-imidazo[4,5-c]quinolin-1-yl)-phenyl]-propionitrile.

5. The method of claim 1, wherein the PI3 kinase inhibitor is 8-(6-methoxy-pyridin-3-yl)-3-methyl-1-(4-piperazin-1-yl-3-trifluoromethyl-phenyl)-1,3-dihydro-imidazo[4,5-c]quinolin-2-one.

6. The method of claim 1, wherein the patient has medulloblastoma.

7. The method of claim 1, wherein the patient has glioblastoma.

8. The method of claim 1, wherein the patient has glioma.

9. A method for treating Hedgehog pathway related breast cancer, pancreatic cancer or colorectal cancer in a patient in need thereof comprising administering to the patient a Smoothened inhibitor and a PI3 kinase inhibitor, wherein the Smoothened inhibitor is 2-methyl-4'-trifluoromethoxy-biphenyl-3-carboxylic acid [6-(cis-2,6-dimethyl-morpholin-4-yl)-pyridin-3-yl]-amide or a pharmaceutically acceptable salt thereof and the PI3 kinase inhibitor is 5-(2,6-di-morpholin-4-yl-pyrimidin-4-yl)-4-trifluoromethyl-pyridin-2-ylamine, 2-methyl-2-[4-(3-methyl-2-oxo-8-quinolin-3-yl-2,3-dihydro-imidazo[4,5-c]quinolin-I-yl)-phenyl]-propionitrile, or 8-(6-methoxy-pyridin-3-yl)-3-methyl-1-(4-piperazin-1-yl-3-trifluoromethyl-phenyl)-I,3-dihydro-imidazo[4,5-c]quinolin-2-one, or a pharmaceutically acceptable salt thereof.

10. The method of claim 1, wherein the patient has breast cancer.

11. The method of claim 1, wherein the patient has pancreatic cancer.

12. The method of claim 1, wherein the patient has colorectal cancer.

* * * * *